(12) United States Patent
Lewis et al.

(10) Patent No.: US 6,426,225 B1
(45) Date of Patent: Jul. 30, 2002

(54) METHOD OF CALIBRATING A VIAL AUTOSAMPLER

(75) Inventors: Edmund T. Lewis, West Chester; Thomas B. Green, Batavia; Harry W. Schmidt, Fairfield; Larry J. DaPrato; Greg J. Herman, both of Cincinatti; Michael A. Hill, Goshen, all of OH (US)

(73) Assignee: Tekmar Company, Cincinnati, OH (US)

( * ) Notice: Subject to any disclaimer, the term of this patent is extended or adjusted under 35 U.S.C. 154(b) by 0 days.

(21) Appl. No.: 09/375,233

(22) Filed: Aug. 16, 1999

Related U.S. Application Data

(60) Division of application No. 08/920,685, filed on Aug. 29, 1997, now Pat. No. 5,948,360, which is a continuation of application No. 08/501,198, filed on Jul. 11, 1995, now abandoned, which is a continuation-in-part of application No. 08/273,537, filed on Jul. 11, 1994, now abandoned.

(51) Int. Cl.⁷ ............................................... G01N 31/00
(52) U.S. Cl. ............................... 436/8; 436/43; 436/48; 436/49; 436/52; 436/53; 436/180; 422/63; 422/65; 422/81; 422/100; 422/104; 702/22; 702/31; 702/32
(58) Field of Search .............................. 422/63, 65, 81, 422/100, 104; 436/43, 47, 48, 49, 52, 53, 180, 8; 702/22, 31, 32; 73/864.23, 864.21

(56) References Cited

U.S. PATENT DOCUMENTS

| 2,541,272 A | 2/1951 | Murphy | ........................ 226/19 |
| 3,912,456 A | 10/1975 | Young | |

(List continued on next page.)

FOREIGN PATENT DOCUMENTS

| EP | 0 635 713 A1 | 1/1995 |
| EP | 0 637 713 A1 | 1/1995 |

(List continued on next page.)

OTHER PUBLICATIONS

O.I. Corporation Model 4460A Sample Concentrator Manual table of contests page and pp. 9, 61–64, and pp. 85–101 (admitted prior art—published at least as early as Jul. 1, 1993.

Article by M. Markelov et al. entitled "Automation of Multiple Analytical Procedures in an Industrial Laboratory . . . ", from *Advances in Laboratory Automation Robotics 1985*, pp. 209–230.

(List continued on next page.)

*Primary Examiner*—Maureen M. Wallenhorst
(74) *Attorney, Agent, or Firm*—Westman, Champlin & Kelly, P.A.

(57) ABSTRACT

A modular vial autosampler has a storage area for vials containing samples to be analyzed and at least one modular sampling station. A vial transfer mechanism includes an arm having a gripper that lifts a sample vial from the storage section, and the arm moves it to a station for identification and then to a sampling station, and under central control activates the sampling station for obtaining a sample for analysis. The vial transfer mechanism gripper is movable in X, Y, and Z directions to capture and move a selected vial and includes an alignment guide for the vials. Potentiometers are used for providing signals indicating arm position and the control is provided with updated information for calibration of the potentiometers and also updated position information for the arm relative to a fixed home position is obtained.

18 Claims, 18 Drawing Sheets

U.S. PATENT DOCUMENTS

| | | | |
|---|---|---|---|
| 4,070,284 A | 1/1978 | Fujita et al. | 210/31 C |
| 4,094,197 A | 6/1978 | Harris, Sr. et al. | |
| 4,095,472 A | 6/1978 | Mowery, Jr. | |
| 4,112,743 A | 9/1978 | Mowery, Jr. | 73/61.1 C |
| 4,200,607 A | 4/1980 | Suzuki | 422/64 |
| 4,279,860 A | 7/1981 | Smolen | 422/63 |
| 4,313,735 A | 2/1982 | Yamashita et al. | 23/230 |
| 4,342,341 A | 8/1982 | Lee | 141/1 |
| 4,359,891 A | 11/1982 | Ahlstrom, Jr. et al. | 73/23.1 |
| 4,476,733 A | 10/1984 | Chlosta et al. | 73/863.91 |
| 4,478,095 A | 10/1984 | Bradley et al. | 73/864.21 |
| 4,520,108 A | 5/1985 | Yoshida et al. | 436/52 |
| 4,532,969 A | 8/1985 | Kwaan | 141/27 |
| 4,536,199 A | 8/1985 | Toon | 55/67 |
| 4,558,603 A | 12/1985 | Closta et al. | 73/864.21 |
| 4,578,244 A | 3/1986 | Cosgrove, Jr. et al. | 422/65 |
| 4,622,457 A | 11/1986 | Bradley et al. | 235/464 |
| 4,680,270 A | 7/1987 | Mitsumaki et al. | 436/52 |
| 4,699,718 A | 10/1987 | Jones et al. | 210/659 |
| 4,710,355 A | 12/1987 | Ushikubo | 422/100 |
| 4,713,974 A | 12/1987 | Stone | 73/864.23 |
| 4,754,657 A | 7/1988 | Schneider | 73/866 |
| 4,816,730 A * | 3/1989 | Wilhelm, Jr. et al. | 318/568.22 |
| 4,890,930 A | 1/1990 | Nohso | 366/208 |
| 4,920,056 A | 4/1990 | Dasgepta | 436/50 |
| 4,924,716 A | 5/1990 | Schneider | 73/866 |
| 4,944,781 A | 7/1990 | Ruggirello et al. | 55/386 |
| 4,969,993 A | 11/1990 | Nash, Jr. et al. | 210/198.2 |
| 5,012,845 A | 5/1991 | Averette | 141/329 |
| 5,042,293 A | 8/1991 | Heyde | 73/61.1 |
| 5,080,864 A | 1/1992 | Shaw | 422/62 |
| 5,094,961 A | 3/1992 | del Valle et al. | 436/180 |
| 5,096,670 A | 3/1992 | Harris et al. | 422/62 |
| 5,100,557 A | 3/1992 | Nogami et al. | 210/634 |
| 5,108,705 A | 4/1992 | Rounbehler et al. | 422/65 |
| 5,147,551 A | 9/1992 | Averette | 210/640 |
| 5,152,176 A | 10/1992 | Bryselbout et al. | 73/23.41 |
| 5,158,748 A | 10/1992 | Obi et al. | 422/100 |
| 5,158,895 A | 10/1992 | Ashihara et al. | 436/526 |
| 5,254,311 A | 10/1993 | Ushikubo | 422/81 |
| 5,260,028 A | 11/1993 | Astle | 422/81 |
| 5,262,049 A | 11/1993 | Ferkany | 210/258 |
| 5,277,871 A | 1/1994 | Fujii et al. | 422/70 |
| 5,308,583 A | 5/1994 | Sanuki | 422/100 |
| 5,316,954 A | 5/1994 | Hupe et al. | 436/89 |
| 5,380,486 A | 1/1995 | Anami | 422/63 |
| 5,384,093 A | 1/1995 | Ootani et al. | 210/656 |
| 5,393,434 A | 2/1995 | Hutchins et al. | 210/656 |
| 5,403,386 A | 4/1995 | Collier et al. | 96/105 |
| 5,417,922 A | 5/1995 | Markin et al. | 422/65 |
| 5,424,037 A | 6/1995 | Zimmerman et al. | 422/64 |
| 5,427,743 A | 6/1995 | Markin | 422/104 |
| 5,432,098 A | 7/1995 | Wilks | 436/161 |
| 5,436,166 A | 7/1995 | Ito et al. | 436/161 |
| 5,455,006 A | 10/1995 | Aota et al. | 422/63 |
| 5,462,660 A | 10/1995 | Singleton et al. | 210/198.2 |
| 5,468,643 A | 11/1995 | Su et al. | 436/161 |
| 5,472,669 A | 12/1995 | Miki et al. | 422/63 |
| 5,483,843 A | 1/1996 | Miller et al. | 736/864.23 |
| 5,525,298 A | 6/1996 | Anami | 422/63 |
| 5,578,495 A | 11/1996 | Wilks | 436/178 |
| 5,948,360 A * | 9/1999 | Rao et al. | 422/65 |
| 5,993,744 A * | 11/1999 | Rao et al. | 422/103 |
| 5,998,217 A * | 12/1999 | Rao et al. | 436/179 |
| 6,040,186 A * | 3/2000 | Lewis et al. | 436/53 |
| 6,056,921 A * | 5/2000 | Rao et al. | 422/65 |
| 6,143,573 A * | 11/2000 | Rao et al. | 436/180 |

FOREIGN PATENT DOCUMENTS

| | | |
|---|---|---|
| JP | 60-42959 | 2/1985 |
| JP | 60-79135 | 6/1985 |
| JP | 62-162647 | 10/1987 |
| JP | 59-192957 | 11/1994 |
| WO | WO 91/13350 | 9/1991 |
| WO | WO 92/05448 | 4/1992 |
| WO | WO 92/15 875 | 9/1992 |

OTHER PUBLICATIONS

Article by M. Markelov et al. entitled "Analysis of Water and Soils for Trace Organic Contamination via Headspace and Purge and Trap Techniques Using Robots", from the Proceedings of the Tenth Annual Symposium of the U.S. environmental protection Agency Office of Water (May 13–14, 1987), pp. 248–266.

Article by F. Jones entitled "Automatic Samplers for Gas Chromatography" from JJ J Chromatographic Science (Dec. 1980) pp. 664–669.

Five one–page sheets from Dynatech Precision Sampling Corp. entitled "PTA–30", "PTA–30W/S", "DYNASOILS", "DYNAWATERS", and "DYNATRAP" (all undated).

A brochure from Dynatech Precision Sampling Corp. entitled "PTA–30W/S AUTOSAMPLER", dated Jul. 1993.

Operating manual for "PTA–30", dated 5/88.

Operating manual for "PTA–30", dated 5/90.

A brochure by Tekmar Company entitled Concentrating on Tomorrow's Chromatography Today (undated).

A brochure by Tekmar Company entitled "2000 Series Concentrator Systems . . . " (undated).

Selected pages from "Catalog 94–96" by Tekmar Company (undated).

A brochure from Dynatech Precision Sampling Corp. entitled "Introducing DynaWaters", dated 2/92.

A brochure from Dynatech Precision Sampling Corp. entitled "Introducing DynaSoils", dated Jul. 30, 1993.

Tekmar TekNote, "Glassware Options for Purge & Trap Concentrators", by J. Twachtman and E. Heggs, Winter 1994, vol. 3.3, pp. 1–3.

"Theory of Purge and Trap Gas Chromatography Purge Efficiency" pp. 3–5, publication date believed to be 1 year prior to effective date of filing this application.

Set of drawings of needle for Aquatek 50 labeled Aquatek 1 through Aquatek 5, illustrating public use structure as of May 6, 1994. (admitted prior art).

"Automatic Methods of Analysis," Valcárcel et al., Techniques and Instrumentation in Analytical Chemistry, vol. 9, 1988.

Aquatek 50 User Manual—Tekmar Company, pp. 1–5; through 3–9; 4–7 through 4–13; 5–25 through 5–36, drawings of Aquatek 50 namely right interior; right top interior components and lower left interior copenents; and Aquatek 50 flow diagrams for prepurge; sample pressure #1 or #2; empty vial; and backflush needle. Published May 6, 1994. (admitted prior art).

Three drawings 7000–2 and 7000–3 showing needle in PCT Publication WO 91/13350—in public use at least by Sep. 5, 1991.

Drawing labeled 2016–1 showing needle; believed publically available at least as early as Jan. 31, 1994. (admitted prior art).

ALS 2016/ALS 2032 User Manual—Tekmar Company, pages bearing ALS2016 front view and upper right view; pp. 21, 22, 54, 55, 66, 67, 68 and pages bearing sample heater positioning diagram; ¾ Glassware Diagram and Drawings No. 14–3236–000 and flow diagram, publication revised Jan. 31, 1994. (admitted prior art).

* cited by examiner

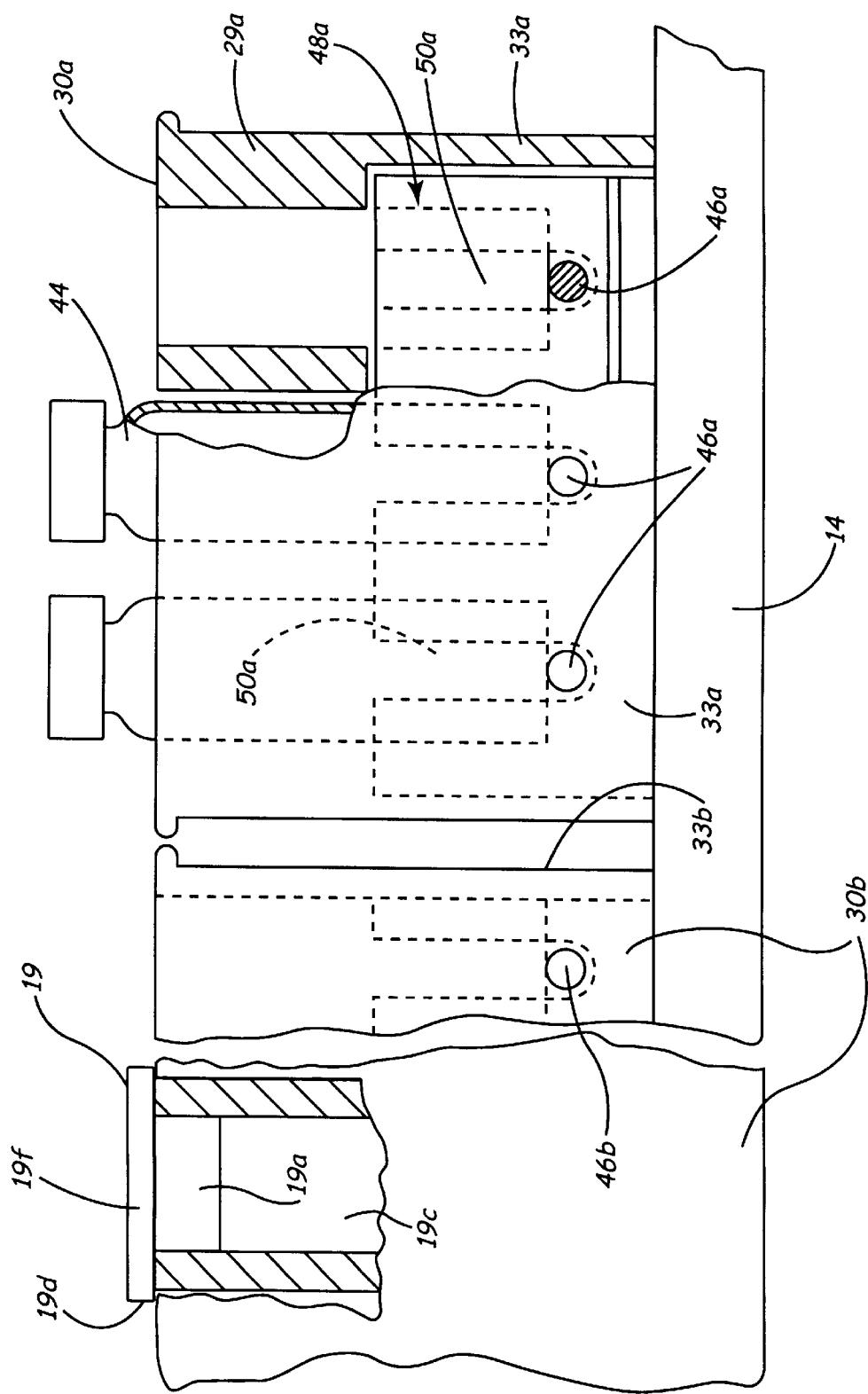

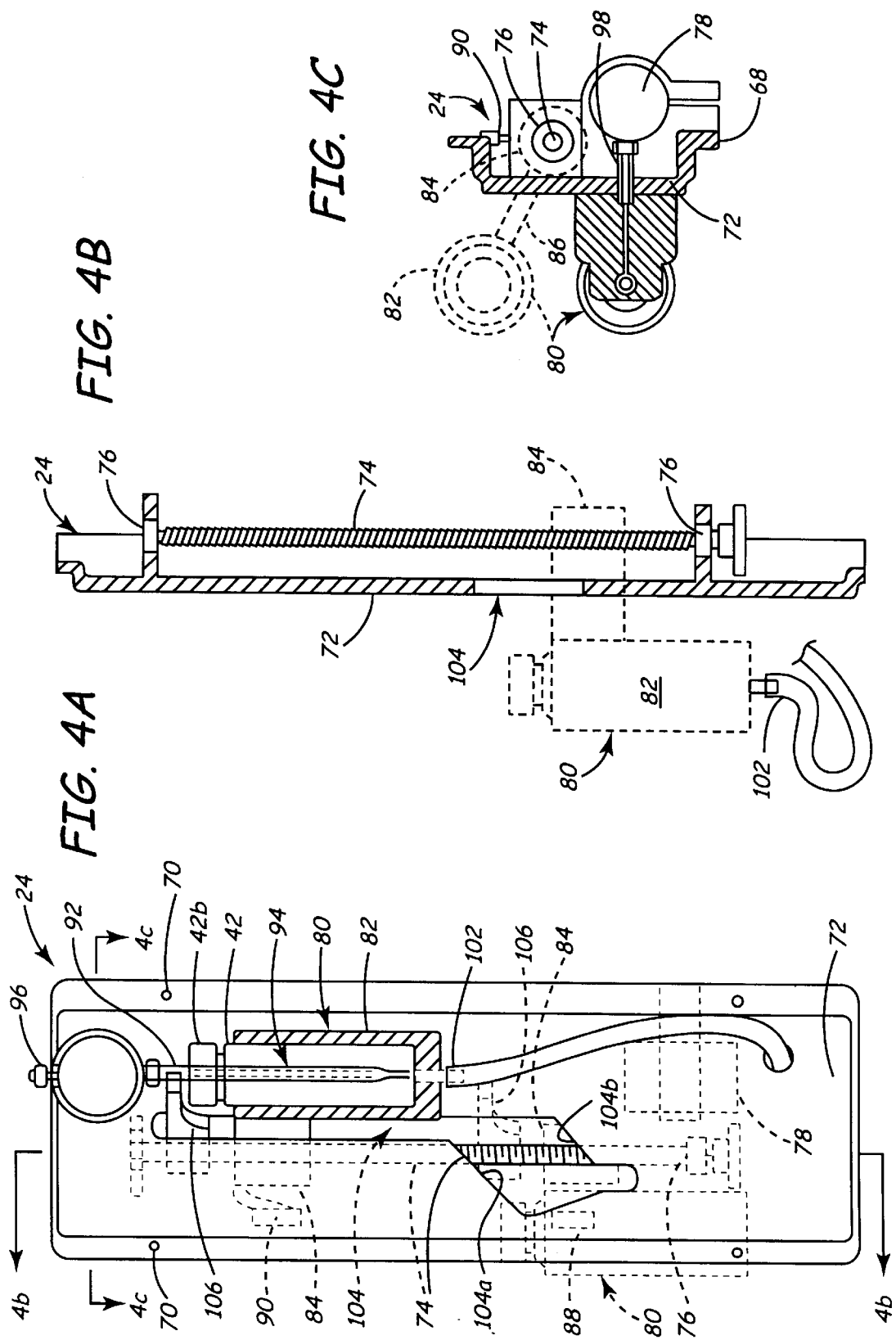

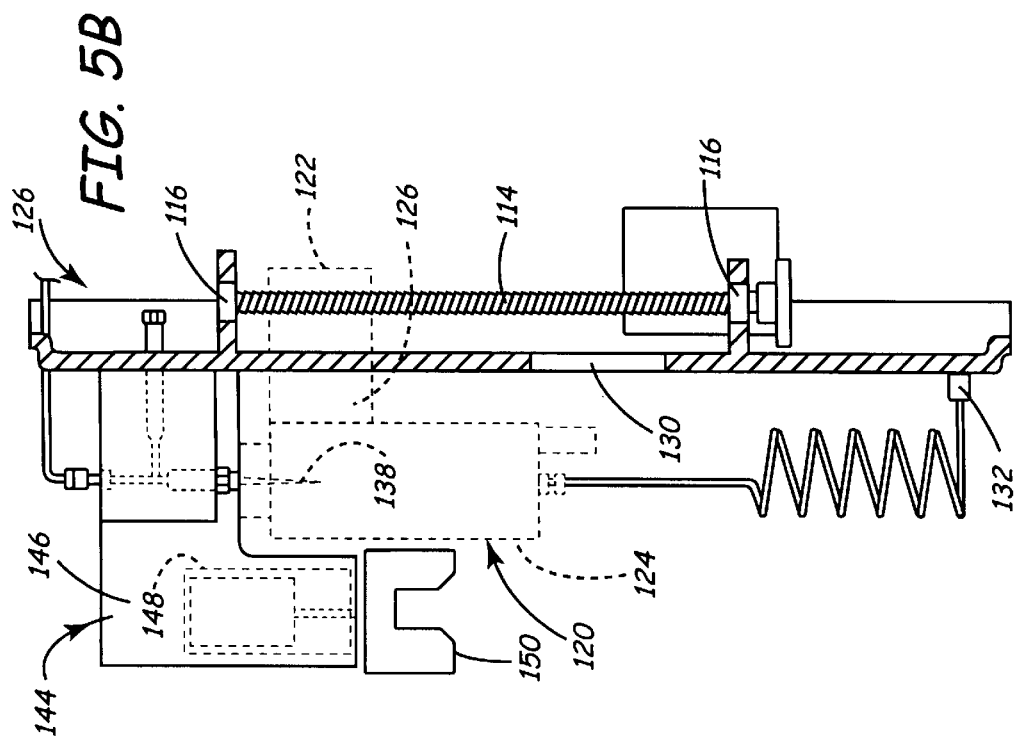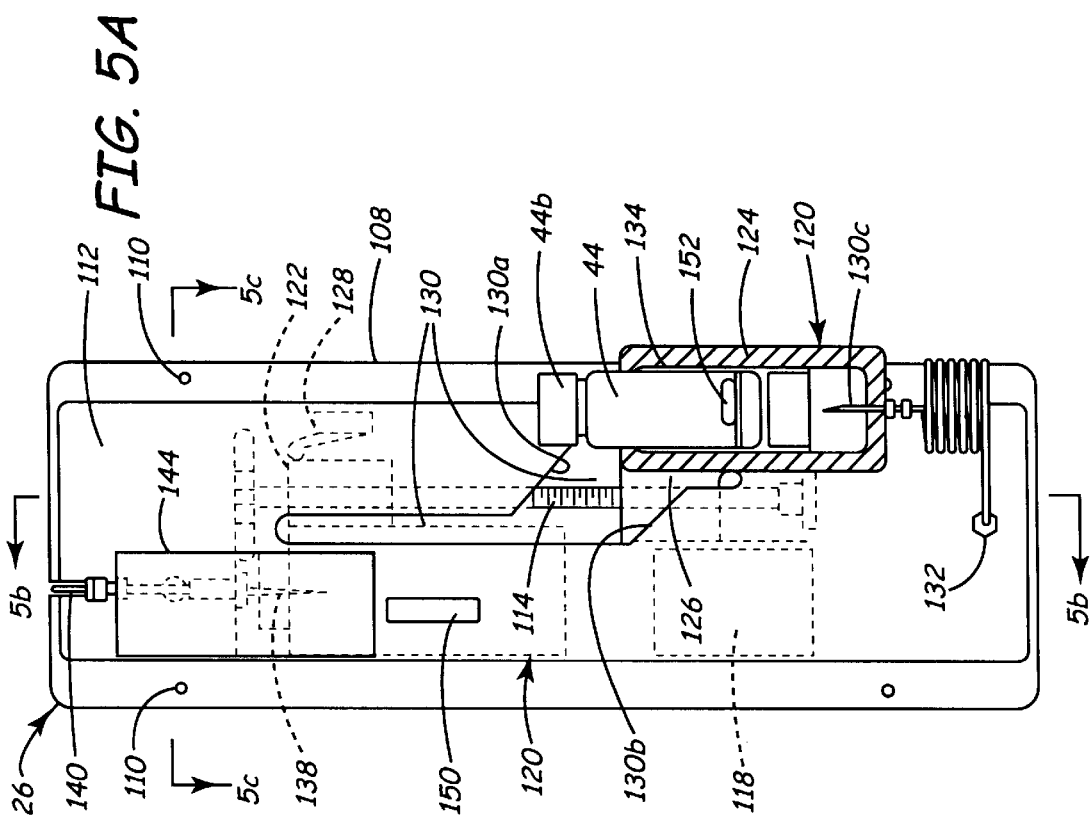

METHOD OF CALIBRATING A VIAL AUTOSAMPLER

CROSS REFERENCE TO RELATED APPLICATION

This application is a divisional application of application Ser. No. 08/920,685, filed Aug. 29, 1997, now U.S. Pat. No. 5,948,360 issued Sep. 27, 1999, which is a continuation of application Ser. No. 08/501,198 filed Jul. 11, 1995, now abandoned which is a continuation-in-part of application Ser. No. 08/273,537, filed Jul. 11, 1994 now abandoned.

BACKGROUND OF THE INVENTION

The present invention relates to a machine that handles vials containing chemical specimens or samples and moves vials from storage trays to one or more sample stations on the machine under software control.

Gas chromatographs and similar chemical species analyzers such as mass spectrometers are known. Vial handling machines, such as the model 7000 Headspace Autosampler sold by Tekmar Co., Cincinnati, Ohio, USA, are also known. The model 7000 extracts from a covered vial a predetermined amount of fluid from a static gaseous headspace above a sample, and conveys the predetermined amount of fluid (containing volatiles to be identified) to a gas chromatograph. Vial autosamplers using dynamic headspace techniques are also known, such as the model PTA-30W/S Autosampler sold by Dynatech Precision Sampling Corp., Baton Rouge, La., USA. The model PTA-30W/S routes a purge gas into a covered vial containing a sample, and provides an outlet from the vial to carry the exiting fluid (comprising the purge gas and volatile components from the sample) to a separate concentrator trap unit.

SUMMARY OF THE INVENTION

In one aspect of the present invention, a vial handling device comprises a base unit and a sampling module adapted to mate with the base unit. The vial handling device has a vial storage area on the base unit to hold multiple vials in known locations, and a sampling station in the sampling module where fluid is removed from the vial. The vial transporter has a controlled arm with a vial gripper for moving a vial between the storage area and the sampling station. The sampling module has a needle assembly to penetrate the vial to remove the fluid, and mates with the base unit proximate the sampling station. In a preferred embodiment, the base unit has two sampling stations.

The vial transporter arm projects from the base unit along a first (Y) axis, and the main arm is adapted for translation along a second (X) axis substantially perpendicular to the first axis. The vial transporter also includes a vial gripper head assembly adapted for movement along the main arm in the Y axis. The vial gripper assembly includes a gripper head adapted for translation along a third (Z) axis substantially perpendicular to the first and second axes. The position of the gripper assembly and gripper head in the X and Y directions are sensed by potentiometers which are used to provide position information. The indicated position of the gripper assembly is calibrated relative to a known reference such as a fixed home position each time the autosampler is started, or at operator selected times, to insure accurate positioning of the vial transporter. The travel of the gripper assembly is sensed with suitable sensors, as disclosed beam interrupters that will provide position information relating to a known mechanical calibration position on the base unit. The gripper assembly scale along its X and Y axes between sensed limits is calibrated by determining a digital count from the analog voltage from the position indicating potentiometers and correlating that count to the known distance between limits. Software adjustments are made as required to the scale (counts per inch) for the X and Y axes so that the positioning system for the vial transporter stays in calibration.

Additionally, the vial storage area utilizes trays or racks that have receptacles for the vials to be stored and moved to various stations for the vials and ultimately to the sampling modules. A calibration system is utilized in connection with the gripper assembly with position sensors for determining the orthogonality of the storage trays or racks, using a mechanical sensing bar positioned in each of the racks (two racks are used preferably) and by determining the actual Y axis location of an edge of the calibration bar. The position identifiers, such as look-up tables in a microprocessor or computer that provide the X-Y coordinates of each of the vial receptacles in the racks, are modified to accommodate any slight skewing of the respective rack.

Another aspect of the invention is an improved stabilizing mechanism for the vials which are held by the gripper head and then lifted and moved. Gripper fingers are used for grasping the neck and cap of the vial, and a stabilizing ring surrounds the main part of the vial as the gripper head lifts the vial. The stabilizing or guide ring retracts as the gripper head moves to engage a vial in a rack when the vial is to be moved, to permit gripping the vial and then the ring extends under spring load to surround the vial so that cocking or other misalignment of the vial relative to the gripper head axis will be reduced or eliminated so that the vial will be properly orientated for placing into a vial holder station on the base, for example, a sampling station.

A series of sequentially controlled valves, coupled with a syringe type pump provides for the analysis of samples removed from the vials placed in the sampling station.

A vial handling device in the sampling station moves a vial having a specimen therein from a loading site where it is placed by the gripper head, to a sampling site, and includes a carrier adapted to hold the vial, an elevator coupled to the carrier, and a mechanism to translate the carrier laterally as the vial is transported from the loading site to the sampling site.

In another aspect of the invention, an autosampler device includes a base unit having a port therein, a central control circuit including a removable circuit module disposed proximate the port, and a panel which is sized and movably held to the base unit to alternately cover and expose the port, thereby providing access to the removable circuit module through the port.

BRIEF DESCRIPTION OF THE DRAWINGS

FIG. 3a is a fragmentary end view of a vial rack assembly with parts broken away to show a thermal block;

FIGS. 4a–4c are front, side sectional, and top sectional views, respectively, of a first sampling module in accordance with the invention;

FIGS. 5a–5c are front, side sectional, and top sectional views, respectively, of a second sampling module in accordance with the invention;

FIG. 5d is an enlarged sectional view of a vial holder assembly in FIG. 5a;

FIG. 6b is a sectional view taken along line 6b—6b in FIG. 6a;

For convenience, items in the figures having the same reference symbol are the same or serve the same or a similar function.

DETAILED DESCRIPTION OF THE PREFERRED EMBODIMENTS

Figure 1:
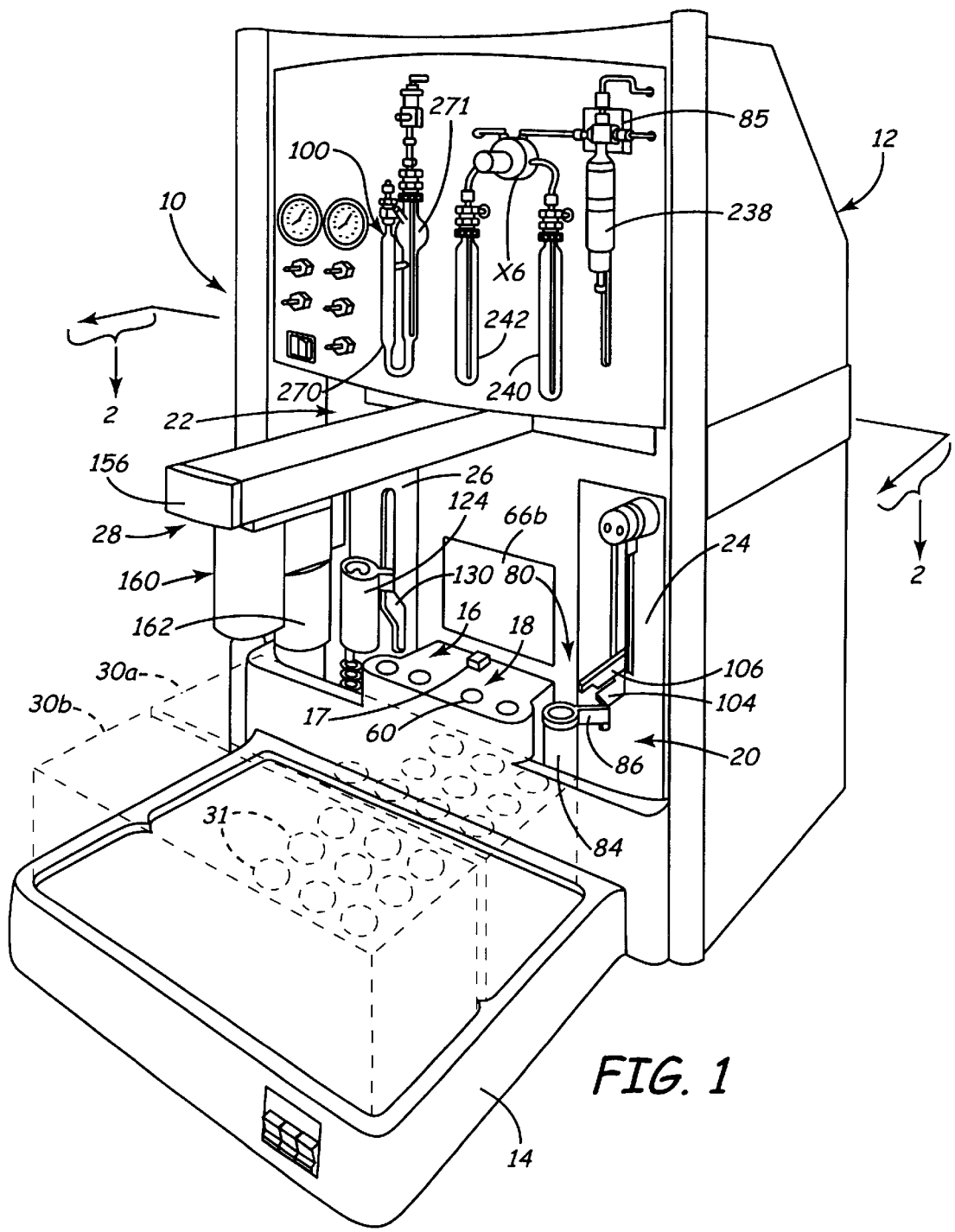
FIG. 1 is a perspective view of a vial autosampler device in accordance with the invention.

FIG. 1 shows a perspective view of a vial autosampler device 10 in accordance with the invention. The device 10 includes a base unit 12 that includes a vial storage platform area 14, a vial equilibration station 16, a vial identification station 18, separate first and second sampling stations 20 and 22, and a fluid handling system comprising valves, glasswork, and other fluid handling components. Device 10 also includes separate first and second sampling modules 24 and 26 each detachably mounted to the base unit 12 at sampling stations 20,22, respectively. Each sampling module 24 and 26 receives a vial containing a specimen and extracts a fluid from the vial for further analysis. Device 10 also includes a vial transporter 28 that carries individual vials between vial storage area 14, vial equilibration station 16, vial identification station 18, and the first and second sampling stations 20,22. Finally, device 10 includes a central programmable control circuit that accepts user inputs and controls the operation of device 10.

Figure 2:
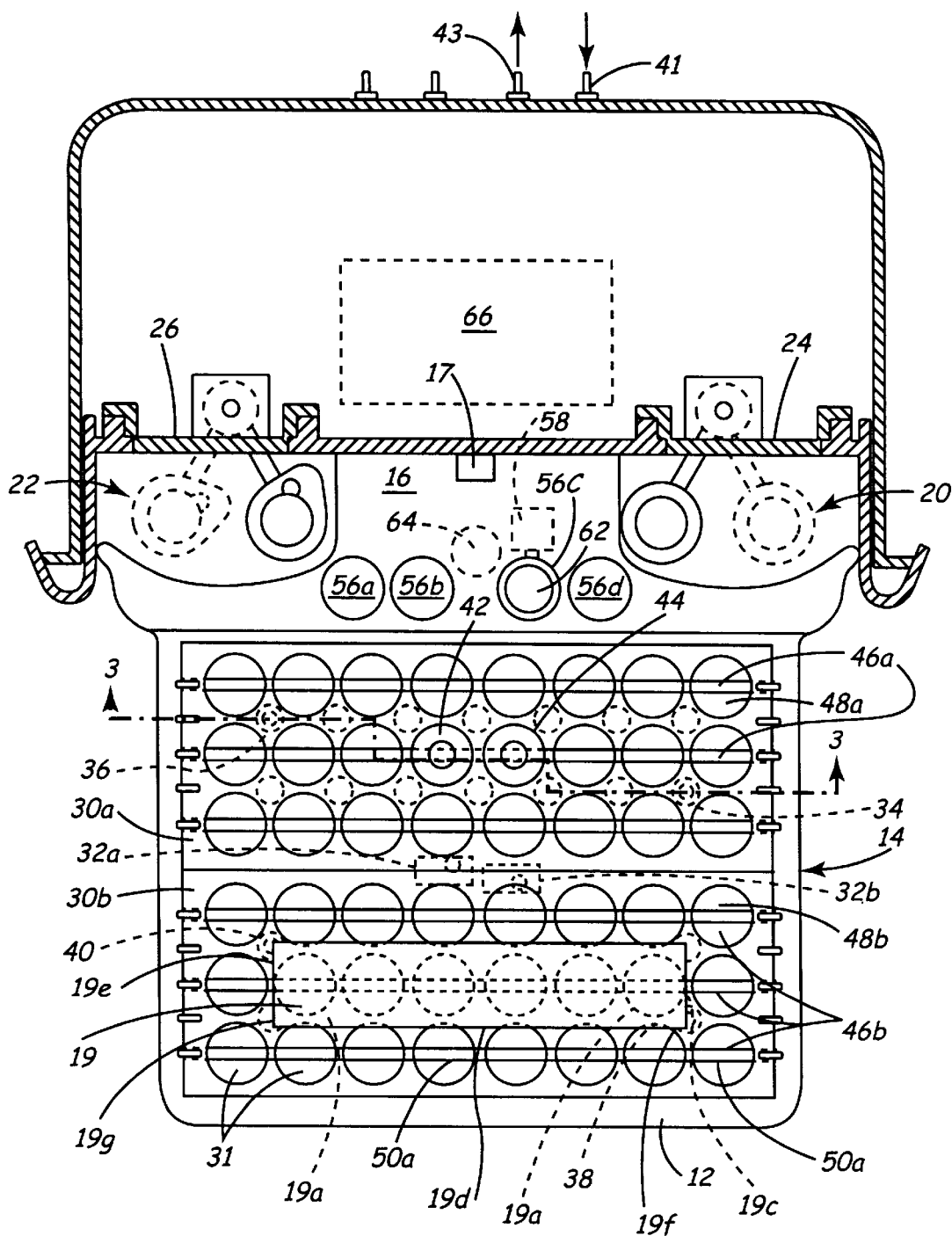
FIG. 2 is a cut-away view of the device of FIG. 1 along plane 2—2, with only key components shown and with some components shown in block form.

FIG. 2 shows a cutaway view of device 10 as taken along line 2—2 in FIG. 1. Vial storage area 14 includes a fixed or stationary platform shaped to receive removable vial racks 30a, 30b, which vial racks are preferably substantially identical. Specimen-containing vials can be loaded into pockets or receptacles 31 of racks 30a, 30b at a separate location and kept in storage until needed. The racks 30a, 30b each include upper portions 29a, 29b, and peripheral skirts 33a, 33b that support metal cross rods 46a, 46b. The rods 46a, 46b extend across the racks and are spaced below the upper portions 29a, 29b. The rods align with each pocket 31 and support the ends of vials placed in the pockets 31. When ready for testing, one or both of the loaded racks can be lowered into position at vial storage platform area 14. Included in vial storage platform area 14 are two push-button switches 32a, 32b positioned on the platform to detect the presence of racks 30a, 30b respectively. In each case, the weight of the loaded rack causes the rack skirt to depress the push-button to change the state of the switch.

Preferably, the skirts of racks 30a, 30b slide down over thermal blocks 48a, 48b (one for each rack) which are fixedly mounted to vial storage platform area 14. The thermal blocks 48a, 48b have internal cavities or passageways 49 therein for fluid circulation. The cavities 49 are accessible from below the thermal blocks 48a, 48b by fittings 34,36,38,40. (See FIGS. 2 and 3) Base unit 12 has an input fluid port 41 and a drain port 43 connected by internal tubing (not shown) to the fittings for a fluid circuit as follows as shown for thermal block 48a in FIG. 3: user-supplied fluid, such as tap water, enters port 41 and enters the cavity 49 of the thermal block underneath vial holder 30a through fitting 34; the fluid drains via fitting 36 from that cavity and enters the cavity of the thermal block 48b underneath holder 30b through fitting 38; the fluid then exits the cavity via fitting 40 and leaves device 10 via drain port 43.

Figure 3:
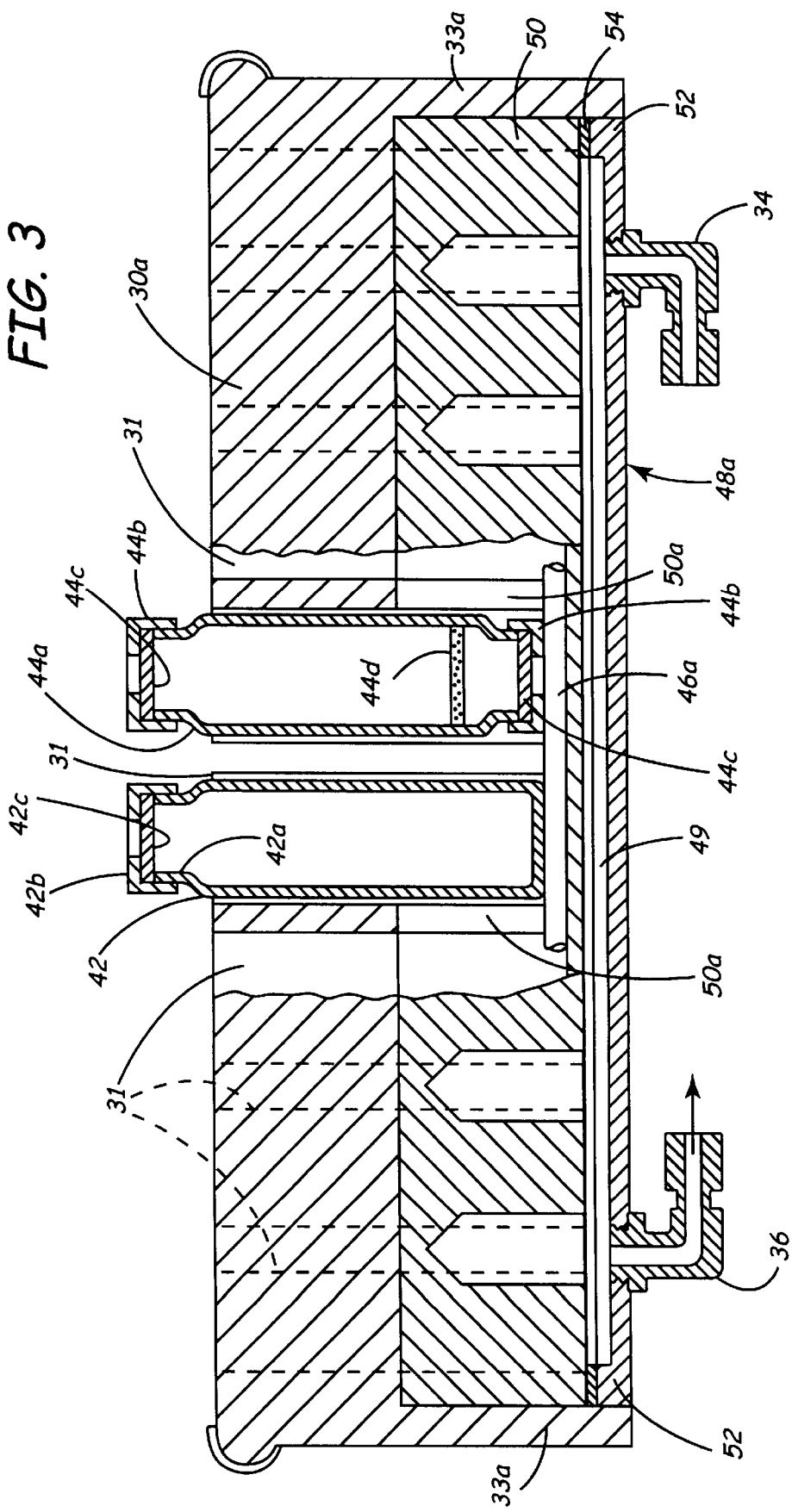
FIG. 3 is a sectional view of a vial rack along line 3—3 in FIG. 2.

Only a few of the vial receiving pockets or receptacles 31 of the rack/thermal block combination are shown occupied by specimen containing vials in FIGS. 2 and 3. Vial receiving pockets or receptacles 31 accept either a vial 42 having a single end cap 42b or a vial 44 having end caps 44b at each end. Vials 44 as shown in FIG. 3, preferably have a liquid retaining, gas porous divider frit 44d dividing each vial into upper and lower chambers. Each end cap can be crimped or, preferably, screwed onto the respective vial end. A septum 42c, 44c respectively, seals the specimen within the vial.

Each thermal block 48a, 48b includes a unitary upper portion 50, a lower portion 52, and a gasket 54 sandwiched therebetween. As shown typically, the internal fluid cavity 49 is formed between upper portion 50 and lower portion 52. Upper portion 50 is preferably composed of a high thermal conductivity material such as aluminum. The lower portion 52 is preferably composed of a low thermal conductivity material such as a suitable plastic to heat isolate the thermal blocks from the rest of base unit 12, thereby reducing thermal transfer to other parts of the base unit and reducing the time required to cool (or heat) the thermal blocks 48a, 48b. Base unit 12 remains at or near ambient temperature.

Channels 50a are cut in upper portion 50 of thermal blocks 48a, 48b to receive the metal rods 46a, 46b (FIG. 3a) so that when rack 30a, 30b rests in place at least the lower portion of each of the vials is substantially surrounded by and in thermal contact with the thermal blocks 48a, 48b. The metal rods 46a, 46b provide additional thermal conduction between the thermal block and the vials.

If desired, vial storage area 14 can comprise a vial-carrying rotating carousel or other known automated vial advancement device in place of the vial racks held stationary in storage area 14. The stationary vial racks allow high packing density of the vials over the entire vial storage area, thereby reducing the cross-sectional area ("footprint") of device 10 for a given number of vial storage positions. A small device footprint is an important consideration in many applications. Further, the use of stationary vial holders simplifies the construction and operation of device 10.

Turning again to FIG. 2, device 10 includes a vial equilibration station 16 that has an upper surface on which a "home" position calibration pad 17 is formed or mounted. The pad 17 is centered on the base unit and, as will be explained, is used for calibrating the position control system for the vial transporter 28. The equilibration station 16 comprises four ports 56a, 56b, 56c, 56d in the base unit 12 where vials can be placed for a programmable period of time to warm up (or cool down) to the ambient room temperature. Port 56c also functions as vial identification station 18. An outer side wall of each vial can have a sticker bearing a unique bar code pattern. An optical bar code reader assembly 58, available commercially and well known, is disposed in base unit 12 and views the side wall of the vial in port 56c through a vertical slot 60 (partially visible in FIG. 1) in the wall surrounding port 56c. A rotatable disk 62 is provided at the bottom of port 56c and is coupled to a stepper motor 64 controlled by a microprocessor based central control circuit 66. When stepper motor 64 rotates disk 62, the vial resting on the disk 62 rotates until the bar code pattern on the vial wall is detected by reader assembly 58 through slot 60. Central control circuit 66 then turns off stepper motor 64.

A vial can be transported by vial transporter 28 from the equilibration area 16 or directly from the vial storage area 14 to one of the sampling stations 20 or 22 where sampling operations are performed. At each of the sampling stations, a fluid is extracted from the vial. At sampling station 20, a liquid sample from a liquid specimen is extracted from the vial for subsequent sparging to remove volatiles from the liquid sample. At sampling station 22, a sample in the form of a gas or vapor is extracted from the vial during a sparging operation, preferably after injecting a liquid into the vial to contact a liquid or solid (e.g. soil) specimen, stirring the resulting mixture, and heating the mixture.

The vial transporter 28 is controlled as to position through controls that will be explained. In addition to home position calibration pad 17, the position of the racks 30a and 30b is preferably measured so the precise location of receptacles 31, corrected for small shifts of rack position, is stored in the program. In FIG. 2 one of a pair of orthogonal sensing bars 19 is shown. Each bar 19 is held in position in a respective one of the racks 30a and 30b with a pair of plugs 19A that fit into receptacles 31, specifically receptacles shown at 19c and 19e. The bar 19 shown is thus held at positions spaced apart in the "X" direction and extend in the "X" direction. The vial transporter uses the bar 19 as a correction or calibration device to calculate the location of the receptacles 31 of racks 30a and 30b with respect to the X and Y axes.

Vial autosampler device 10 includes one or both sampling modules 24,26, which are adapted to mate with base unit 12 proximate sampling stations 20,22, respectively. Advantageously, vial autosampler device 10 can be outfitted with both or only one of the sampling modules, depending on the requirements of the user. If outfitted with only one module, the other module can be added to the device later.

FIGS. 4a–4c show a front, side, and top view of sampling module 24. A plate 68 has mounting holes 70 for mounting by known means, such as screws, to base unit 12 such that a projecting face 72 of plate 68 mates with a rectangular hole in the front face of base unit 12 and is flush with the surrounding front face of base unit 12. Plate 68 carries a ball screw 74 mounted on bearings 76,76, and driven by a motor 78 which is also carried by plate 68. Coupled to ball screw 74 is a vial holder assembly 80 comprising a vial holder cup 82, a spool 84 driven by ball screw 74, and a connecting arm 86. Ball screw 74 and spool 84 together form an elevator which can raise or lower vial holder 82. Limit switches 88,90 are carried by plate 68 and contact spool 84 at the lowest position and highest or raised position, respectively, of vial holder assembly 80. In FIGS. 4a–4c, vial holder assembly 80 is shown in outline in the lowest position and is shown in solid lines (and in FIG. 4a in cross-section) in the highest position. Vial transporter 28 loads and unloads a vial into vial holder 82 at the lowest position. As the elevator raises the vial, a needle assembly 92 punctures the vial septum. Sampling of the vial contents occurs at the highest position, where the needle assembly 92 fully penetrates the vial. Needle assembly 92, well known in the art, has an inner needle with a port at its lower tip and an outer needle having a port higher up at point 94. At the highest position of the vial, the port at 94 remains above the level of the liquid specimen in the vial while the tip of the inner needle is submerged in the liquid specimen. The inner needle communicates with fitting 96, and the outer needle communicates with fitting 98. In operation, a volume of the liquid specimen is drawn through the center needle and conveyed via fitting 96 to a sparger unit 100 (see FIGS. 1 and 10) on base unit 12 or to an external sparger unit.

After a sampling operation, the sample flow path of device 10 permits flushing of the inner needle of assembly 92, with vial holder 82 raised and empty, with wash fluid such as water to reduce carryover by cleaning the inner surfaces of the inner needle. A drain 102 drains the wash fluid expelled from the needle.

Plate 68 has a slot 104 (FIG. 4a and 4b) through which arm 86 extends. The slot 104 has a narrow top portion and a lower portion with cam edges shaped and positioned relative to ball screw 74 to guide connecting arm 86 laterally as spool 84 moves vertically. As a vial and vial holder rise from the lowest position, the arm 86 rides against the cam edge 104a of slot 104. The arm enters the vertical section and the lateral motion of arm 86 and vial holder 82 is substantially complete when the needle assembly 92 penetrates the vial septum. When lowering the cam edge 104b of the slot 104 causes the lateral shift to the dotted position of vial holder 82 in FIG. 4a and 4c. Other known means such as a separate motor or piston can be used to perform the lateral shift. Cam slot 104 and connecting (follower) arm 86 form a simple and reliable mechanism without any additional motor.

A wiper arm 106, on ball screw 74 moves in unison with spool 84 as the screw 74 turns. As vial holder 82 is lowered after sampling, arm 106 pushes down on the vial end cap to strip the needles 92 if friction causes the vial to remain. When the vial holder assembly 80 reaches the lowest position, it can be seen in FIG. 4a arm 106 does not shift laterally because of its higher position on ball screw 74. The space above vial holder 82 is left free and accessible for loading or unloading a vial.

Figure 5C:
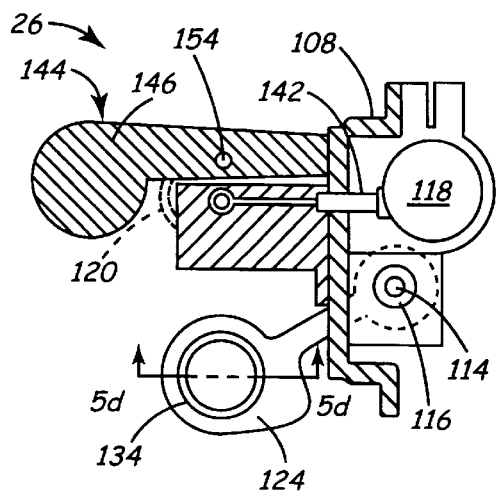
Figure 5D:
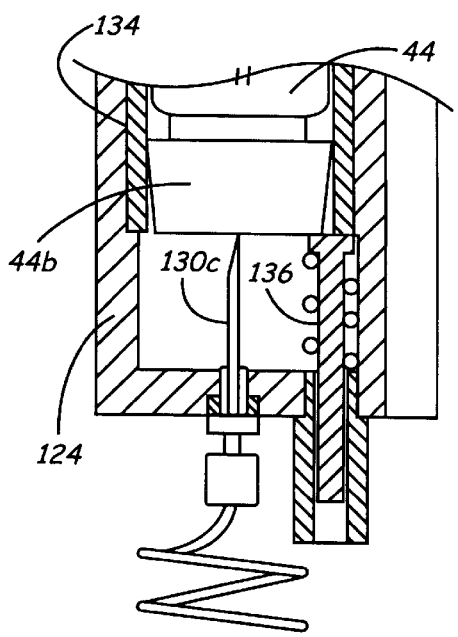

FIGS. 5a–5d show detail of sampling module 26. Module 26 has many elements that have the same function as corresponding elements of module 24. These elements include a plate 108, mounting holes 110, projecting face 112, ball screw 114, bearings 116, motor 118, vial holder assembly 120, spool 122, vial holder 124, connecting arm 126, limit switches 128 (the lower one being hidden behind holder 124 in FIG. 5a), and slot 130 in plate 108. Arm 126 extends through slot 130 and engages the edges 130a or 130b at the lower portion of slot 130 to laterally shift arm 126 and a vial carried in vial holder 124. In FIGS. 5a–5c, the lowest position of the vial holder (shown in solid lines and cross-section) is the vial load/unload position, and the highest position of the vial holder (shown in outline) is the sampling position.

As shown, a hollow lower needle 130c extends through the base of vial holder 120 for puncturing a lower vial septum in a vial 44 having end caps at both ends. Lower needle 130$^c$ fluidically communicates through flexible tubing to fitting 132. Vial holder 124 also has a heating sleeve 134 disposed therein to heat the specimen before or during sampling. Heating sleeve 134 has electrical power provided by wires carried on connecting arm 126 to central control circuit 66. Vial holder 124 also has a spring-loaded plunger 136 operable to keep the lower vial septum above the lower needle 130 when a vial is placed in the vial holder until the vial is raised and sampling occurs, and also to force the lower vial septum off the lower needle 130 after sampling.

Upper needle assembly 138 has an inner and outer needle similar to needle assembly 92, but the needles of assembly 138 are shorter so that their vent ports remain above the expected level of non-gaseous contents of the vial shown. The inner needle of assembly 138 communicates with line 140, and the outer needle communicates with line 142.

Sampling module 26 is further equipped with a magnetic sample stirring mechanism 144. Bracket 146 is affixed to plate 108 and holds a stir motor 148 that turns a primary magnet 150. A bar magnet 152, placed in the vial prior to loading the vial, is thereby induced to spin, mixing the contents of the vial. One type of double end vial useable with sampling module 26 is described in U.S. Pat. No. 5,147,551, herein incorporated by reference, although it is not the only type. Bracket 146 includes a spring-loaded plunger 154 (similar to plunger 136) for urging upper vial septum downward off needle assembly 138.

If either sampling module 24 or 26 is omitted from vial autosampler device 10, a plate can be provided to cover the port on the front panel of base unit 12 that is associated with the omitted module.

Figure 6A:
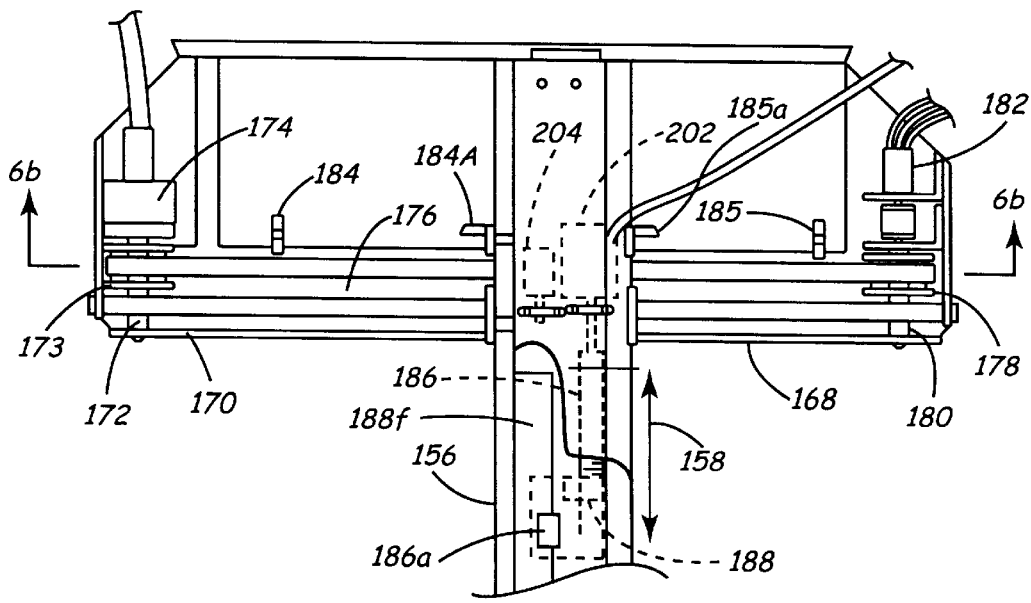
FIG. 6a is a top partial view of a vial transporter according to the invention.
Figure 6B:
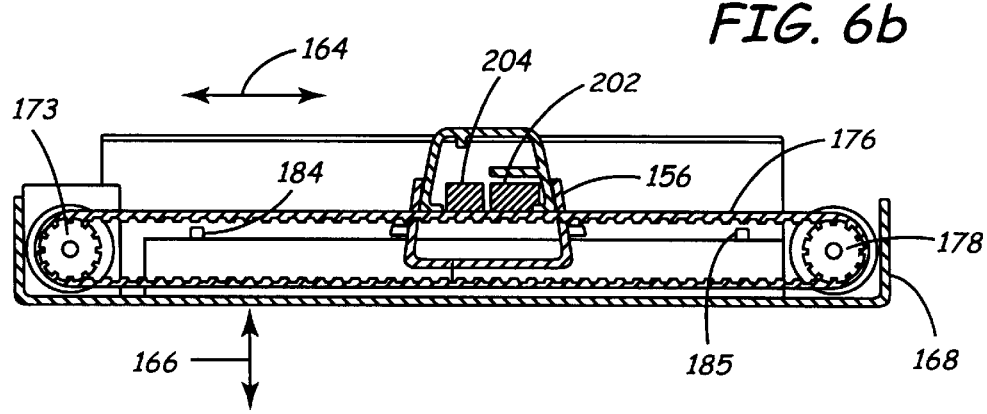
Figure 6C:
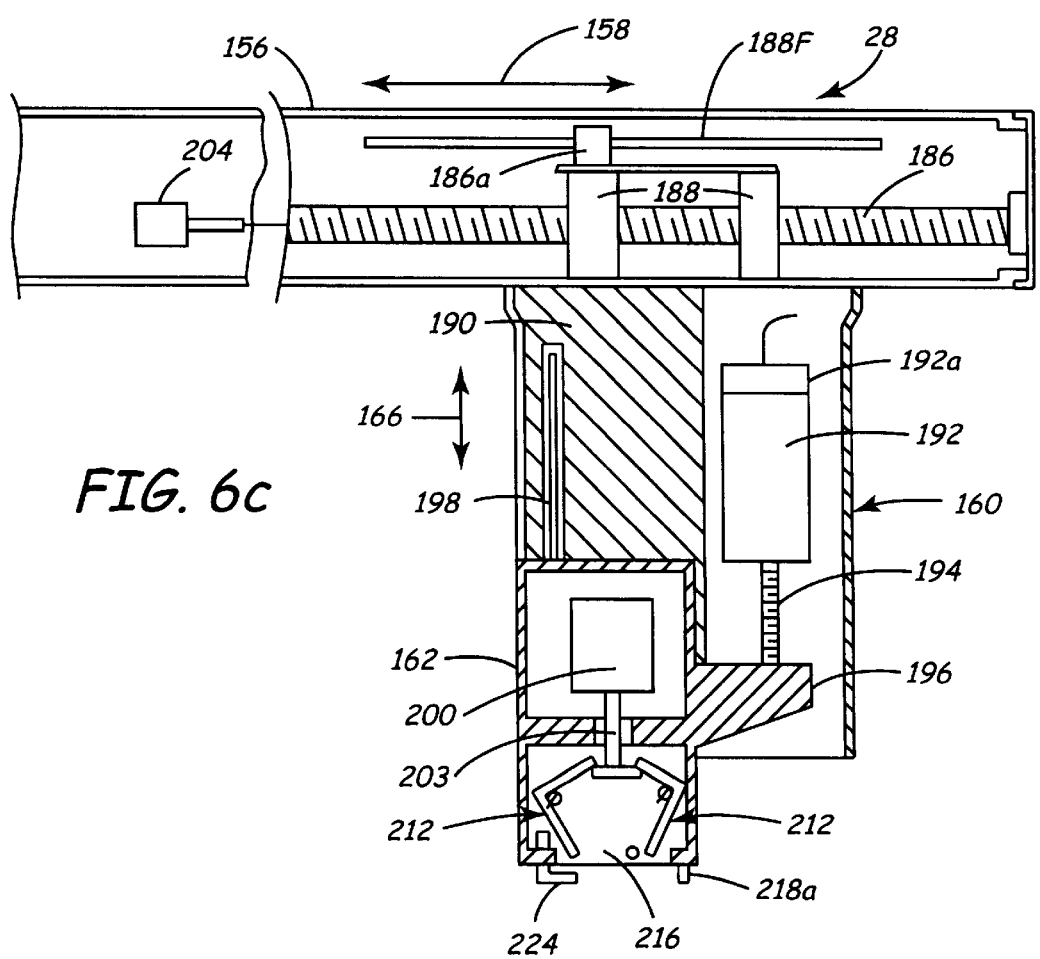
FIG. 6c shows a side sectional view of an end portion of a vial transporter according to the invention.

Another aspect of the invention is the vial transporter 28. Vial transporter 28, controlled by central control circuit 66, moves a vial between vial storage area 14, equilibration station 16, and sampling stations 20 and 22. Referring now to FIGS. 6a–6c, vial transporter 28 includes a main arm 156 extending along a first (Y) axis 158, a vial gripper assembly 160 adapted for movement along main arm 156, and a gripper head 162 which grasps vials by the upper end cap and which can be lowered and raised from gripper assembly 160. Main arm 156 is adapted for movement along a second (X) axis 164, and the motion of gripper head 162 relative to gripper assembly 160 is along a third (Z) axis 166. The first, second, and third axes are substantially mutually perpendicular. Vial transporter 28 includes a tray 168 which is rigidly mounted inside base unit 12 and which supports a suitable circuit board for use with the arm.

The tray 168 forms a module that can be inserted and removed from the base unit 12 so that the main arm 156 can be removed and replaced merely by unplugging the necessary electrical power and signal leads. The tray 168 has a front flange frame member 170 that is used for supporting a shaft 172 and pulley 173, driven from a controllable, variable speed reversible arm drive motor 174. The pulley 173 drives a belt 176 that is mounted over an idler pulley 178 mounted on an idler shaft 180 at an opposite end of the tray 168 from the motor. The idler shaft 180 drives a potentiometer 182 that provides a voltage signal (proportional to its wiper position relative to an end position) indicating the position of arm 156. Arm 156 clamps to belt 176 in a suitable manner, as shown in FIG. 6b, and moves laterally as indicated by the double arrow 164 as the belt 176 is driven. Limit sensors 184 and 185 sense position of the arm 156 and provide signals used by the controller to stop or reverse the motor 174 when the travel limit is reached.

A motor 202 drives screw 186, rotatably mounted in arm 156, as shown in FIG. 6c, and mounts a suitable drive block 188 that supports the gripper head 162. A rotating potentiometer 204 driven by screw 186 provides an output voltage proportional to its wiper position relative to an end position of the potentiometer, and this signal also is compared to a signal representing a desired position to provide an error signal to drive motor 202. An indication of the position of the vial gripper assembly 160 along screw 186 (the Y axis) is thus provided.

The Y axis movement also is marked with end limit signals provided by a sensor 186a. Sensor 186a preferably is a photo-beam sensor comprising a light emitting diode and a light sensitive transistor spaced from the diode. The sensor 186a is mounted on a circuit board supported on the drive block 188. A "flag" 188f, which is a rail or beam like flat blade, is supported on the arm and is positioned so that the flag 188f is between the diode and the transistor of the sensor. The flag 188f is precisely trimmed as to length and when the gripper assembly moves so the sensor clears either end of the flag the state of the sensor 186a changes to provide the end position signal of the gripper assembly.

A gripper head frame 190 is supported on the drive block 188. A drive motor 192 with an encoder 192a drives a vertical, rotatable screw 194 that threads through a lug 196 fixed to the gripper head 162, to move it vertically as guided by a guide rod 198. Gripper head 162 mounts gripping fingers for gripping the tops of vials and for transporting the vials when the main arm 156 or the gripper assembly 160 is moved.

Figure 6D:
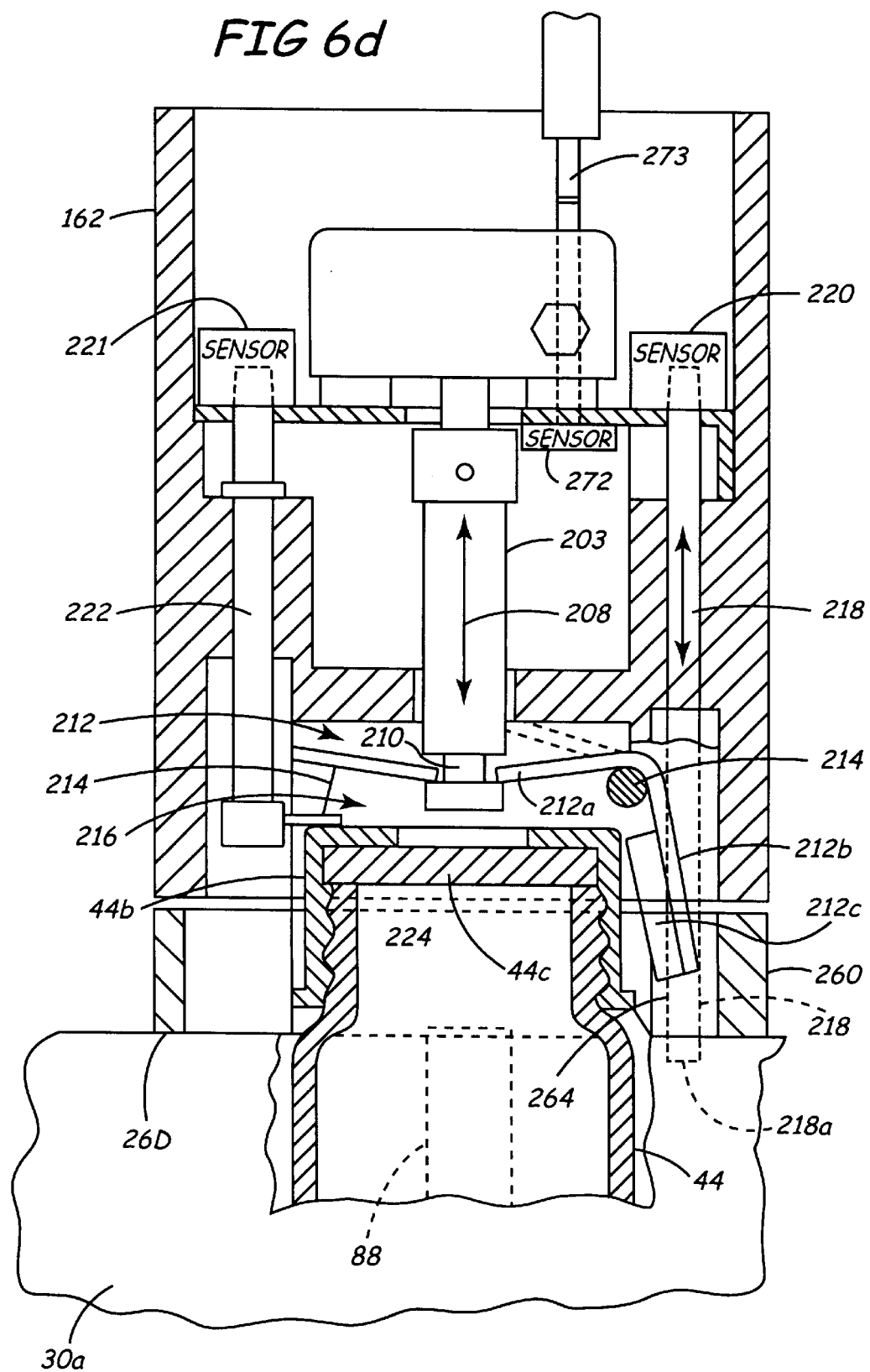
FIG. 6d is an enlarged sectional view of a vial gripper and vial stabilizing and guide ring made according to the present invention with parts broken away.

Referring now to FIG. 6d, a solenoid actuator 200 linearly drives a drive tang 203 in a vertical direction 208. The outer end of tang 203 has an annular groove 210 formed therein. A plurality of gripper fingers 212 are mounted in a lower end 216 cavity of the gripper head, and are L-shaped, with an actuator end 212a that fits into the groove 210. There are at least three of the gripper fingers 212, around the periphery of the gripper head. The fingers are mounted on suitable pivot rods 214 that are fixed in the gripper head 162. The L-shaped gripper fingers 212 have outwardly extending finger ends 212b that include a grip pad 212c. Cavity 216 is of size to receive the upper portion and cap of a vial, as shown in FIG. 6d.

The actuator 200 is spring loaded to lift the ends 212a of the fingers 212 to the grip position shown in dotted lines. The finger ends 212b and the grip pads 212c then grip tightly onto the cap 44b on the neck 44a of a vial 44, so the vial is lifted by operating drive motor 192 through the screw 194.

Figure 6E:
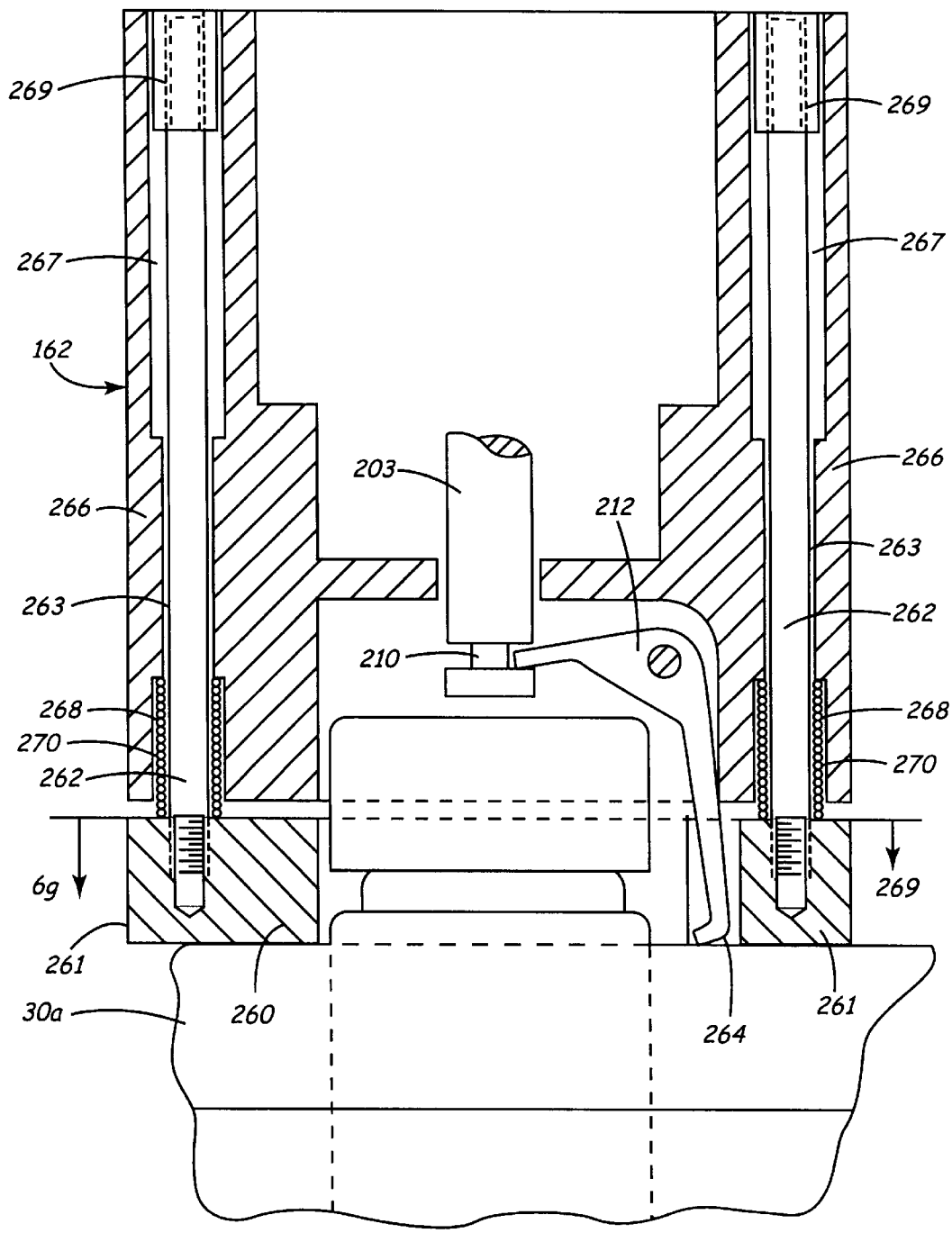
FIG. 6e is an enlarged sectional view of a vial gripper and vial stabilizing and alignment ring taken on a line to illustrate the supports for the vial alignment ring, with the vial gripper in position to grip a vial in a storage tray.
Figure 6F:
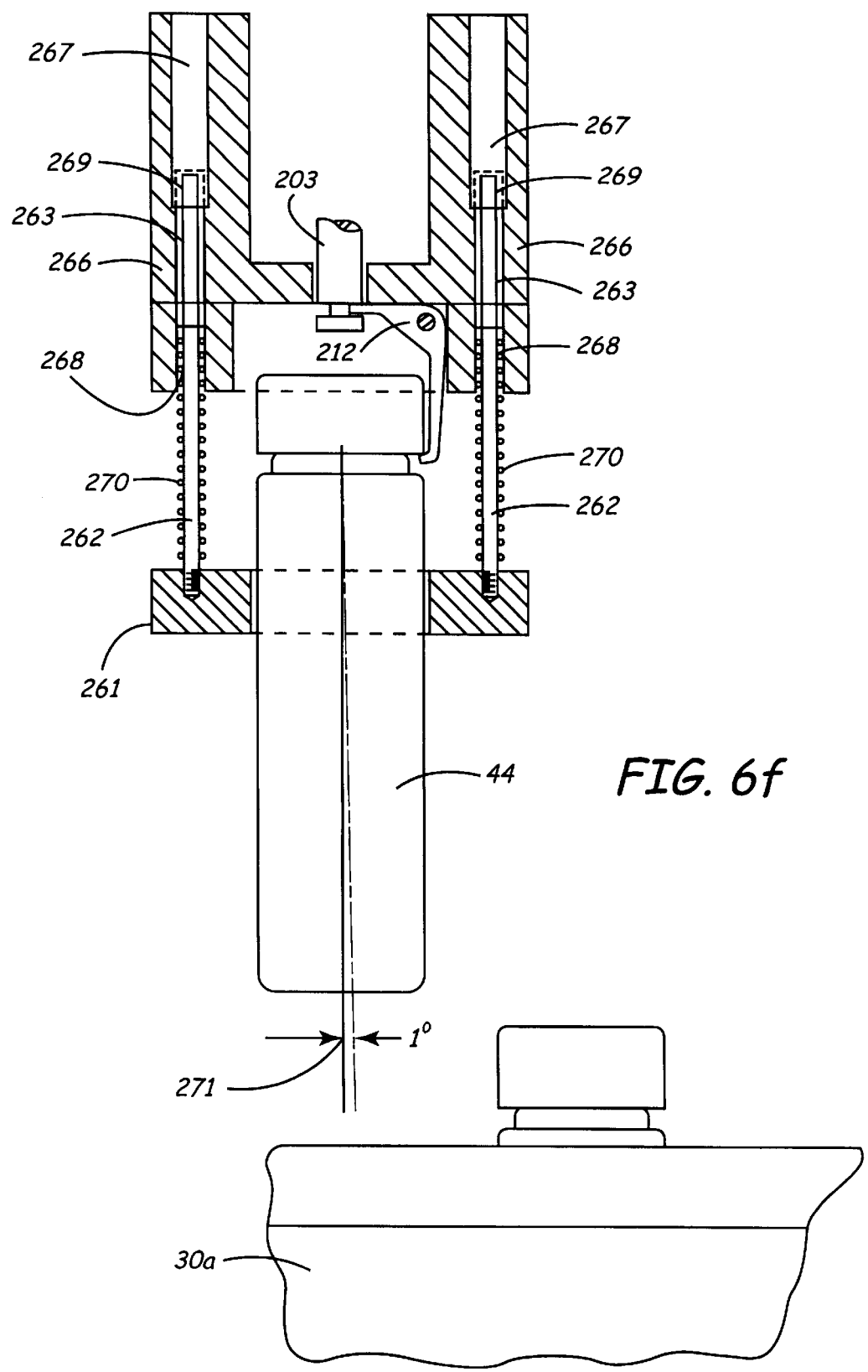
FIG. 6f is a view taken along the same line as FIG. 6e with the gripper head raised and the vial alignment ring in position around the main part of a vial.
Figure 6G:
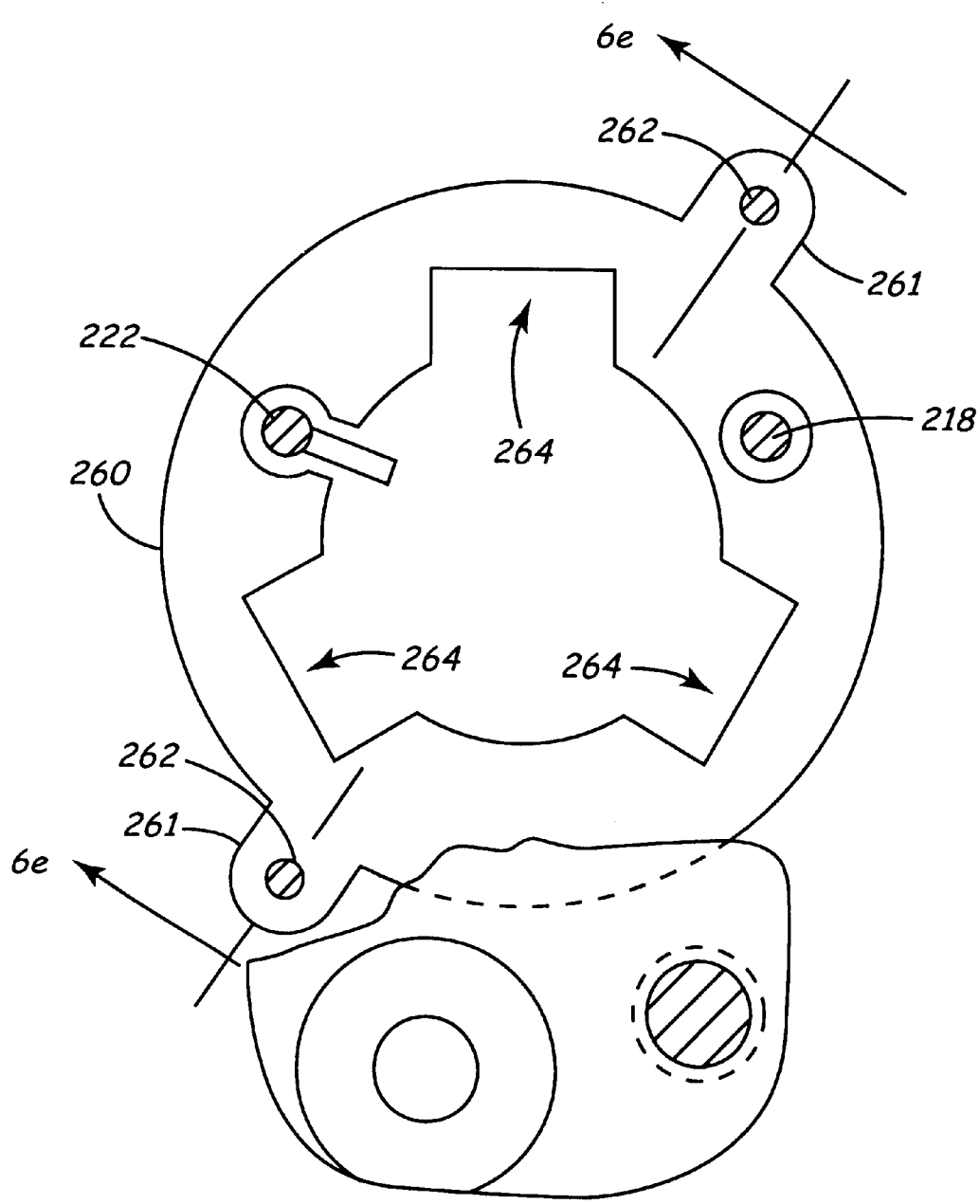
FIG. 6g is a sectional view showing the top of the vial alignment ring and taken on line 6g—6g in FIG. 6f.

In FIG. 6e and 6f, slightly different ends are shown, which act as hooks under the edges of the caps.

The gripper head includes a sliding plunger 218 connected to a switch or sensor 220. When a plunger end 218a contacts the upper portion of a rack 30a, 30b as the gripper head 162 is lowered, the plunger 218 will move, and a signal will be delivered by the sensor 220 indicating the gripper is down. The actuator 200 is energized so the gripper fingers are open. A second plunger 222 is slidably mounted on the gripper head on the side opposite from the plunger 218, and a sensing foot 224 engages the vial cap when a vial is within the gripping fingers 212c. A sensor 221 is actuated by plunger 222. The actuator 200 can then be de-energized so the fingers 212 pivot under spring load to grip a vial.

The signal from sensor 221, indicating the presence of a vial, enables the motor 192 to lift the vial and transport it to the appropriate station under control of central control circuit 66. The gripper head 162 operates to deliver vials to and from the equilibration, identification and respective sampling stations under control of control circuit 66. The signal from sensor 221 also indicates that a vial has been released so that the gripper head can be further operated after a vial is deposited in a vial holder at a sampling station, for example. The gripper head 162 is a fail safe unit and actuator 200 will remain in its gripping position if there is a loss of power to prevent vial breakage.

The gripper fingers 212 of the gripper head 162 are surrounded by a vial alignment ring 260 that serves to align the vial and straighten it if it gets slightly cocked when grasped by the gripper fingers. The ring 260, as shown in FIGS. 6d, 6e, 6f and 6g, has a pair of guide cylinders 261 on opposite sides thereof, and the guide cylinders 261 in turn mount elongated guide pins 262. The ring 260 has recesses 264 for clearing the gripper fingers 212, and also is provided with openings for the plunger 218 and the plunger 222, so that they will operate without interference.

The pins 262 are fixed to cylinders 261 and are slidably received in the bores 263 of guide housings 266 that are mounted onto the gripper head 162. The guide housing 266 has an enlarged bore portion 268 that is of size to received a long compression coil spring 270 that surrounds the respective pin 262. The spring 270 bears upon the upper surface of the cylinders 261 aligned with their respective housing, and provides a spring force urging the ring downwardly away from the bottom of the gripper head 162.

Also, the upper ends of the guide housing have long larger diameter bores 267 which receives a standoff 269 that thread on the ends of the rods 262 to hold the rods on the housing. The standoffs 269 stop travel of the ring 261 as shown in FIG. 6f by engaging a shoulder at the end of bore 263.

As shown schematically in FIG. 6d, when the gripper head 162 is lowered to engage a vial 44 held in one of the vial racks 30a or 30b (rack 30a is shown) the upper surface of the rack will support the ring 261 and the gripper head moves toward the ring 261 as the springs 270 compress. The plunger 218 is shown engaging the upper surface of the rack 30a in FIG. 6d as well, so that the sensor 220 has delivered its signal to indicate that the gripper should be actuated for holding the vial 44 that is shown. In FIG. 6e the gripper finger shown is in an open position.

As the vial 44 is lifted from the receptacle 31, that is as the motor 192 is driven to raise the gripper head 162, the spring loading from the springs 270 will cause the alignment ring 261 to separate from the bottom of the gripper head 162, and to surround and slide down along the vial 44 that is being lifted to its stopped position, as limited by the standoffs 269. This action will tend to keep the vial axis substantially coincidental with the central axis of the gripper fingers, and thus the central axis of the gripper head 162. If the vial is cocked or slightly out of position, it will be straightened by the action of the alignment ring 261 so that when it is placed into a receptacle in the equilibration station 16 or one of the receptacles for the sampling stations, the vial will be aligned appropriately so that placement will not be difficult. A maximum misalignment of only about one degree is allowed. The misalignment is illustrated at 271 in FIG. 6f.

Then, again, when a vial is replaced in a receptacle 31 and the gripper head 162 moves downwardly, the vial alignment ring 261 will be retracted against the action of the springs 270 until such time as the vial is properly positioned in the receptacle and the plunger 218 is actuated.

As can be seen, the recesses 264 provide adequate clearance for the gripper fingers. The respective plungers for sensing the vial and sensing the rack or tray holding the vials extend through appropriate openings in the ring.

The nominal position of each vial receptacle for both vial racks is preprogrammed into the microprocessor control unit 66, in the form of X and Y coordinates. The potentiometers 182 and 204 give the X and Y position respectively of the gripper head. There is a gripper up sensor 272 that cooperates with a plunger 273 mounted on the arm to provide a maximum up signal when the plunger 273 interrupts a beam in the sensor 272. The sensor 272 is a photo beam sensor interrupted by the plunger at the maximum raised portions.

Figure 8:
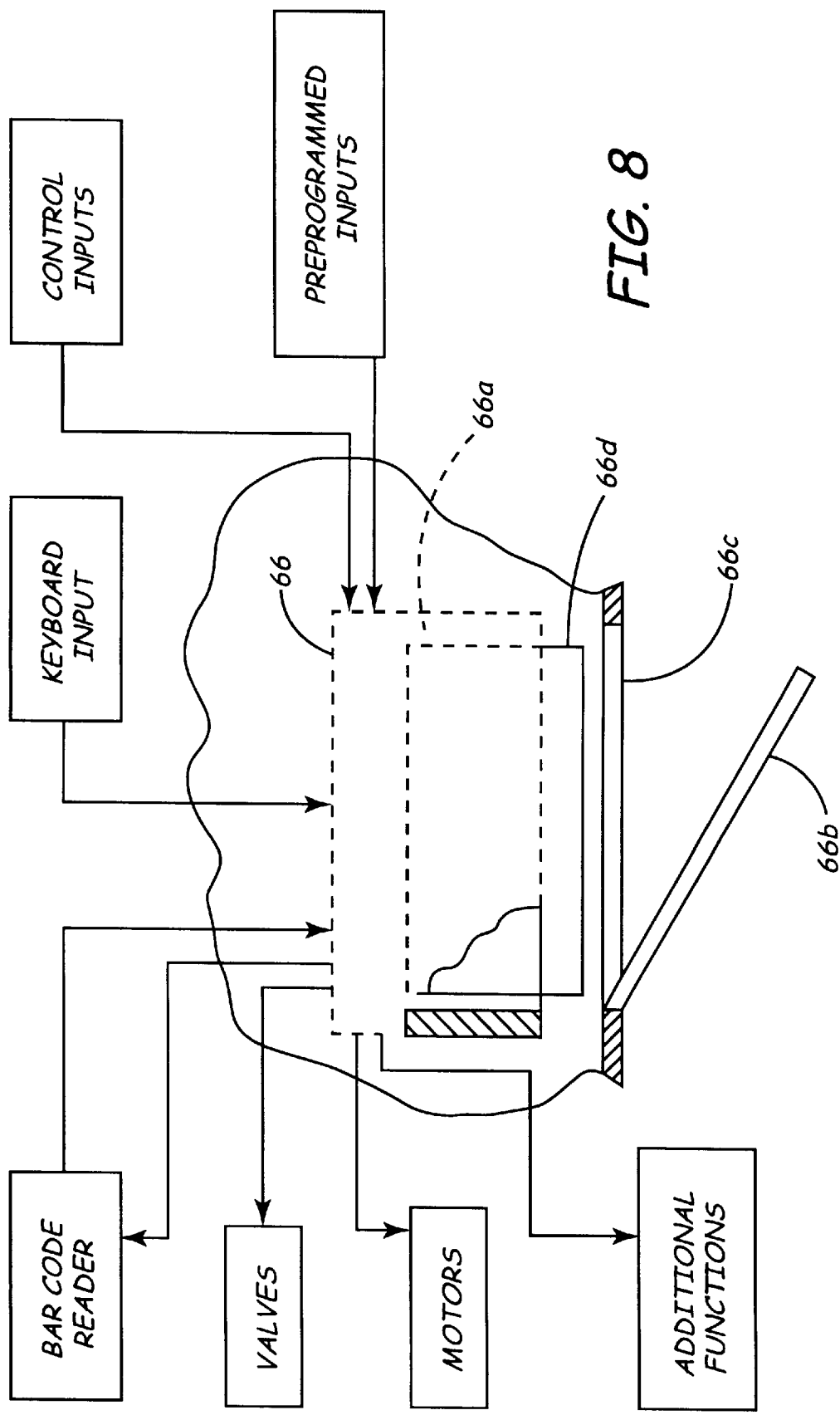
FIG. 8 is a sectional view of an access panel for a control circuit in accordance with the invention.
Figure 11:
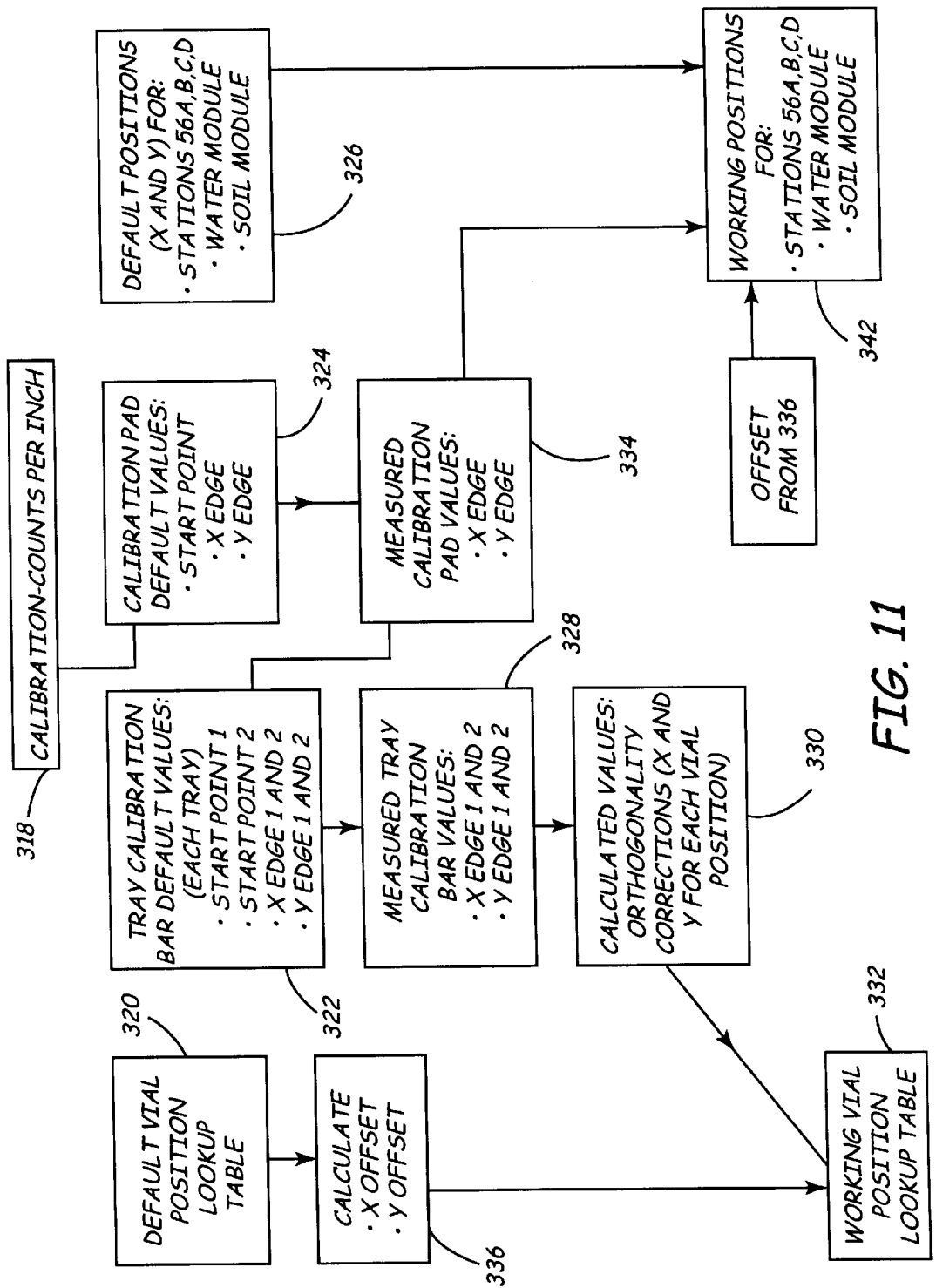
FIG. 11 is a flow diagram of the overall control system used with the robotic arm of the present invention.

Referring to FIG. 8, a schematic representation of an access in the front panel of the base unit is shown, for access to the central control circuit 66 has a plug in slot or port 66a for a removable circuit module such as a microprocessor memory card 66d. An access door 66b shown in both FIGS. 1 and 11 is provided, to open an opening 66c in the front panel of the base unit 12. The opening 66c aligns with the slot for the plug in circuit module 66d that is shown partially removed in FIG. 11, so that for different sampling programs, the memory card or module 66 can be removed and replaced with another module. The access door 66b can have a simple push latch, that will release when pushed, and then latch again when the door is closed. This will permit easy maintenance of various programs for running different samples, utilizing different combinations of the sampling modules that are available without reprogramming.

Figure 9:
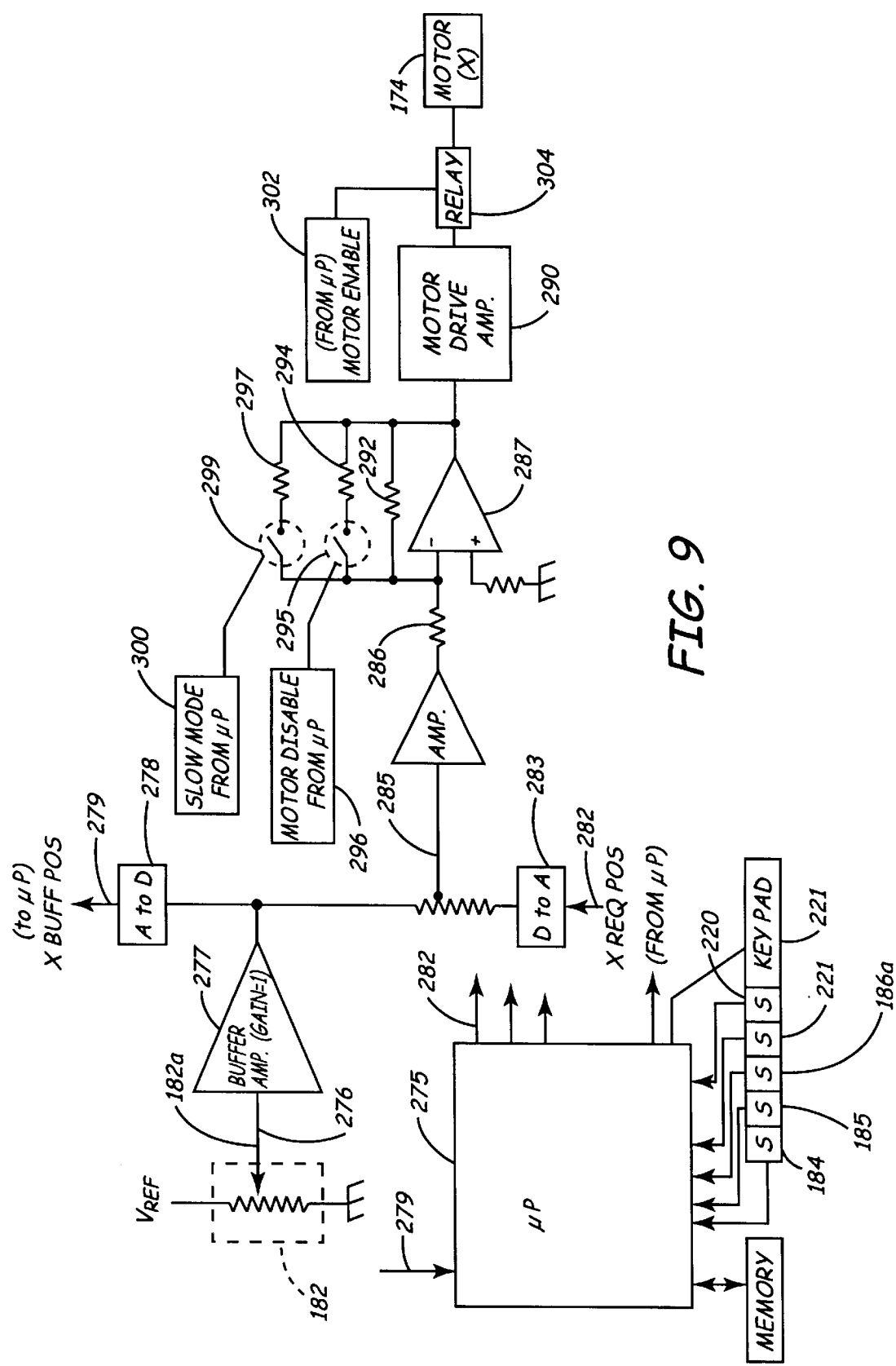
FIG. 9 is a schematic circuit representation for a drive motor circuit for operation of a robotic arm of the present invention.

FIG. 9 illustrates a typical motor circuit that is used in the X and Y drive motors. The central control circuit 66 includes a microprocessor 275 that is programmed appropriately to receive inputs from the various sensors, such as the sensors 184 and 185 for sensing the end positions of the X axis, and the sensors 220 and 221 which are used for the purposes discussed previously.

As stated the Y axis position sensor is provided to signal the end of travel in each direction of movement of the gripper assembly. The end of travel signals for the Y axis are provided to the microprocessor 275. The flag 188f is precision toleranced and is shown in FIGS. 6a and 6c.

The microprocessor 275 is programmed to include suitable command signals for motor energization to drive the motor to move the arm to a desired location. The movement of the arm in the X and Y axes drives a separate potentiometer as was explained, and for illustration purposes the potentiometer used with the X axis motor drive is shown in FIG. 9. This potentiometer 182 has a voltage reference at one end, and a wiper 182a that will provide an output signal along the line 276 to a buffer amplifier 277. This voltage is connected to an analog to digital converter 278 to provide a digital arm position signal to the microprocessor 275 along the line 279. The microprocessor 275 provides an output indicating a requested X axis position from the stored program along the line 282, to a digital to analog converter 283. The inverted analog output is added to the analog output from the buffer amplifier 277 to indicate the actual position along the X axis in FIG. 9. An error signal is thus provided along the line 280. This can be suitable amplified with an amplifier 280. The output of amplifier 285 is connected through a resistor 286 to a motor preamplifier 287.

The preamplifier 287 is used for providing a gain to a motor drive amplifier 290, which ultimately drives the motor, in the showing of FIG. 9, motor 174. Preamplifier 287 has a large valve resistor 292 to provide a high gain. A first substantially smaller valve resistor 294 is connected in parallel with resistor 292 through a switch 295 that functions as a "motor disable" switch controlled by the microprocessor 275 when a suitable motor disable signal is sent as represented by block 296. A "slow mode" switch and arrangement is also shown: an intermediate value resistor 297 is connected in parallel with resistor 292 when a switch 299 is closed in response to a "slow mode" signal from the microprocessor 275. This slow mode signal is represented by the box 300.

By way of example, only the resistor 286 may be 2 k ohms; resistor 292 may be 100 k ohms; resistor 294 may be 10 k ohms and resistor 297 may be 3.3 k ohms, for appropriate operation.

The output of the preamplifier 287 drives the motor drive amplifier 290, whenever a motor enable signal from the microprocessor is received as illustrated by the box 302. The motor enable signal acts through a relay 304 that is part of the motor drive amplifier 290. The correct motor rotational direction is a function of the polarity of the signal from preamplifier 287 so that the motor 174 will be driven either clockwise or counterclockwise as needed, to reach its desired position.

The exact arrangement shown in FIG. 9 can be used for driving the Y axis motor 202 as well, with the suitable input from the microprocessor 275.

Under microprocessor control, the system is set to provide an initial sequence at startup as an automatic routine, to provide for a calibration of the potentiometer outputs, and also to insure that the internal lookup tables as to vial positions in the racks or trays is updated and the correct position for the physical set up that is present are recorded in the memory. The microprocessor 275 includes lookup tables that provides positions for each of the receptacles 31 in the racks 30a and 30b, with respect to a reference position. The reference position in the X and Y directions is determined by the calibration pad 17, and in particular the edges thereof, as measured by a sensor (plunger 218) on the gripping head at startup.

In addition, the racks or trays have to be correctly orthogonally positioned. If not positioned correctly, the lookup table values for the X-Y positions have to be compensated so that for example, if the racks or trays are skewed slightly the center axis of each of the vial receptacles in each row would be slightly different from a default position in both X and Y directions because of the skew.

In order to accomplish the calibration of the system at each start up, a routine has been programmed in the system to first return the gripping head to a home position, where the gripper assembly is retracted near the base of the main arm, and the main arm is centered on the X axis between the sensors 184 and 185. The motor circuits previously described would be energized to match a "home" command.

In order to have an accurate position determination of the gripper head in the X and Y axes, the next routine involves determining the scale of the feedback potentiometers that are used. For example first, the X axis scale will be calculated by energizing the motor 174 to drive belt 176 and move the main arm 156 in a selected direction, toward one of the end limit sensors. For example, the initial drive could be toward the sensor 185 along the X axis. When the sensor 185 indicates that the arm 156 had reached that end point, the motor 174 is reversed and sent at its normal operating speed toward the sensor 184. When sensor 184 is reached, at this point the analog to digital converter value is read by the microprocessor and recorded in memory. The motor 174 is then reversed, and when the sensor 185 is reached, the microprocessor reads the analog to digital value (which reduces in the reverse direction) and records it in memory. The difference of these values determines the potentiometer outpout of voltage value per inch of travel, for convenience, called counts per inch, using a software driven algorithm.

For even more precision a target position or value can be selected and the count from the A/D converter from a reference position to the target is determined and compared to the target value count. The arm can then be moved past the target position to another known start position and reversed so the count to the target coming from the reverse direction is also determined. Differences in the count resulting from the different directions of travel can be averaged to provide a more accurate calibration of the X and Y offset.

For example, if it is known that the distance between the sensors 184 and 185 is ten and one half inches, (and that does not change) the number of counts from the actual position signal from the potentiometer is used for adjusting and updating the scale counts per inch in the operating software so that the X requested position (provided by software) is in harmony with the position provided by the potentiometer. The calibration procedure at every start up to correct for changes in the potentiometers permits the use of potentiometers for position determination, rather than more expensive digital encoders.

Additionally, after calibration in the X axis, the arm 156 is moved to its center or home position in accordance with the program in the microprocessor, and the motor 202 is then energized to cause the gripping head to travel along the screw 186 so that the sensor 186a passes one end of flag 188f. The motor 202 is reversed and the voltage from the potentiometer is converted and when the opposite end of the flag 188f is reached the value is stored in memory. The motor 202 is again reversed and the micro processor reads the analog to digital output of the potentiometer 204 until the first end of the flag 188f is again reached. The difference of the values from the potentiometer determines the counts per inch of travel, through a software algorithm. This calibration routine can be initiated by operator input at the keypad as well.

The gripper mechanism is then lowered by energizing motor 192 until the indicator or plunger 218 rests on the top of the pad 17. The tolerances of the system are such that bringing the gripping head back to this home position is generally within tolerance so that the end 218a of the plunger 218 will rest on the top surface of the calibration pad 17.

The arm motors are then operated, when the plunger end 218a is riding on the surface of the calibration pad 17, at the slow rate of motor operation, that is in a slow mode, along the X axis until the plunger 218 drops off the sharp edge of the calibration pad 17. The calibration pad 17 is made with vertical walls and sharp edges (non chamfered) so that there is an abrupt change of position of the plunger 218 as it moves in the X axis. This is a known position that the edge of the calibration pad 17 which is used to update the home position in the X direction for the arm 156. The calculation from the edge to the center of the calibration pad 17 is done by software update.

Then, once the plunger 218 is returned to the center of the pad 17 or to some other home position that is known, the Y axis motor 202 is energized in a slow mode and the gripper head is moved along the screw 186 until the plunger 218 again drops off an edge of the calibration pad 17. The controls have a known position in the Y direction to use as a reference and to update the software for determining the home or reference position for the arm. The home reference is the reference from which the X-Y position of each of the vial receptacles is set in the lookup tables. Of course, when the unit is moved so that the plunger 218 is placed back onto the pad 17, the gripper head motor would be driven to raise the plunger 218 sufficiently so that it would not catch the edge of the calibration pad 17 and then subsequently relower before the Y axis calibration is made.

Figure 10:
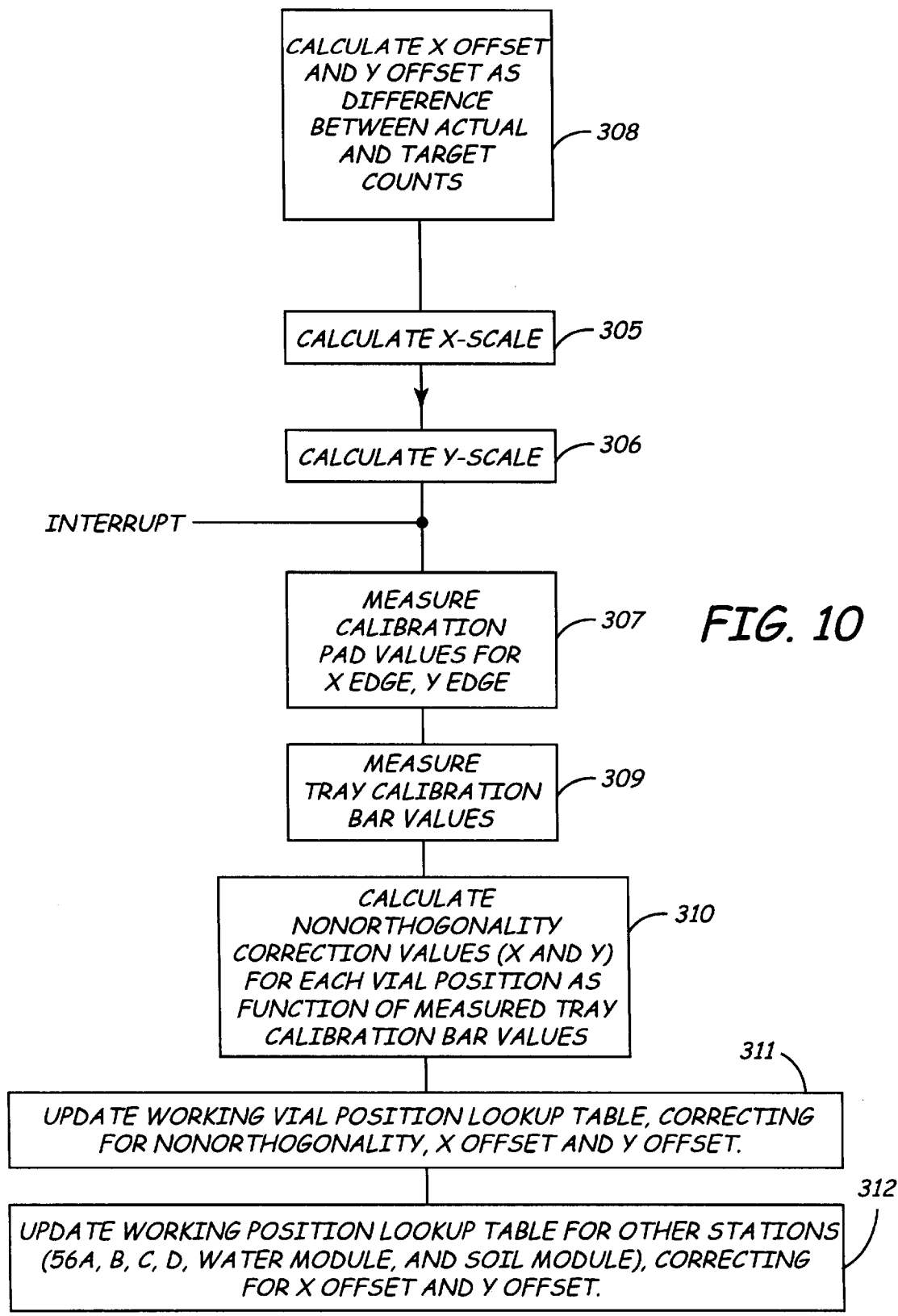
FIG. 10 is a flow diagram illustrating the steps of calibrating the positions of various components of the system.

The steps of this program are illustrated in FIG. 10. In the program the first step is to obtain the X and Y offset values for the actual operation, which are the differences in each axis between the theoretical X, Y coordinates of a location, such as the home position, that is preprogrammed in the look up table provided, and the measured position as determined by the output of the potentiometers. The theoretical or target are default values, and are based upon the theoretical position in the X,Y coordinate system from the original layout. This step is illustrated in block 308. The offset values are used to establish corrections for a working look up table in microprocessor memory. The calculated X scale is shown at 305, and the calculated Y scale is shown at 306, which are them established. These values are obtained as previously described to obtain the counts per inch in each of the axes. The interrupt in the sequence is at the time that the gripper head is moved to its home position on the calibrating pad 17.

Then the measuring of the calibration pad values illustrated at 307 is as described. The X offset and Y offset are used to correct the default or theoretical home position to establish a corrected home position for the X edge and Y edge of the calibration pad 17, respectively.

After that is done, and the new default home position has been established in the software, each of the trays or racks 30a and 30b is inspected, using the calibration bar 19 that was previously explained, for orthogonal positioning to make sure that the rows of vial receptacles are parallel to the X axis, or, if offset or skewed, make a compensating adjustment in the software and updating of the default positions lookup tables for each of the receptacles. Referring to FIG. 2, where the orthogonal calibration bar 19 is shown in only one of the trays or racks for the vials, for illustrative purposes, the main robot arm 156 would be driven in an X direction to a location laterally that would be close to one of the ends of the calibration bar 19, and then the gripper head 162 would be driven along the screw 186 to a location where the plunger 218 would rest on the top of the calibration bar 19. That could be done for example by providing the X-Y coordinates from the software lookup table for the receptacle illustrated at 19c in FIG. 2 which supports one of the plugs 19a.

Then by moving the gripper head 162 back toward the base of the main arm until the plunger 218 drops off the sharply defined edge of the bar 19 that is shown at 19b, a first reference distance from the home position in the Y direction can be obtained for the lookup tables. The information will be stored until the opposite end of the calibration bar 19 is inspected for example, adjacent the receptacle shown in dotted lines as 19e. The gripper head is raised, moved laterally to the end adjacent the receptacle 19e and then lowered down so the plunger rests on the top of the bar 19, after which the gripper head is retracted toward the base of the arm until the plunger 218 drops off the edge 19d adjacent the receptacle 19e. This position information is recorded and compared to the information for the position of the edge 19d adjacent receptacle 19c. By comparing these values, the skew or orthogonality status of the rack or tray that has been placed on the support 12 is determined. Also the value of the Y distance to the bar and thus the trays is provided for update, if needed. Appropriate compensation factors can be placed into the lookup table to clearly establish the present position of each of the receptacles for holding the vials.

The X position of the receptacle in each tray or rack 30a or 30b that is the distance in the X direction from the arm center position can be established by using the gripper head plunger 218 to sense the ends of the bar 19 at the corners of the bar. The skew and the actual X-Y position of the receptacles in thus obtained. While the bar is illustrated only in tray 30b in FIG. 2, the bar 19 would also be used to calibrate the positions of the receptacles in the tray 30a as well. In FIG. 10, this step is illustrated at blocks 309, 310 and 311.

Also as shown in FIG. 2, the equilibration receptacles or stations 56a, 56b, 56c and 56d have known theoretical or default X-Y coordinate positions stored in software, and the positions of these receptacles in relation to the operation of the present device is updated. The water module and soil module vial receptacles, which will be loaded with the robot arm also have known positions and in the vial loading position of each of the modules as shown in FIG. 2, will be updated in the software as to their X-Y locations taking into account the calibration sequence just described. This step is illustrated in box 312.

It should be noted that the updating of the lookup tables can be done on a "global" scale where the lookup tables are updated immediately upon calculation of the X and Y axes offsets, and used as a working look up table or the correction factors can be added into the output of the lookup tables for each vial receptacle 31, as well as for the other receptacles 56a–56d and the soil and water module vial holders only during the time when a particular vial receptacle is to be reached.

FIG. 11 provides a flow diagram generally outlining the software operations in the microprocessor 275, for operations as just described. The first step again is to calibrate the scale of the X and Y movements, in counts per inch or other unit of measurement as shown by the block 318 so the correct values will be provided for the subsequent functions.

There is in the memory of the microprocessor and software a default, target or theoretical present value in a lookup table for each of the vial positions for the receptacles 31 of each of the trays or racks and the other receptacles for vials provided. That is indicated at box 320. The X axis offset and the Y axis offset are calculated for position information, as shown by the block or box 336.

Also, the software contains the positions (box 322) of the tray calibration bar 19 for each of the two trays or racks 30a and 30b, and they would have default values in the X and Y directions for the ends of the bars 19 such as that shown adjacent receptacle 19c and adjacent receptacle 19e. It is to be understood that a similar bar would be used on the other tray or rack. The X-Y positions measured for the two ends of bar 19 as sensed by the plunger 218 are illustrated at block 322.

The calibration pad 17 has default position values as illustrated in block 324, including the start point position, which would be the uncalibrated "home" position to which the unit would be returned for calibration, and the X edge and Y edge positions in the X and Y directions, respectively, which is a mechanical position used for establishing the reference point. There would be default positions in the X and Y directions for the stations 56a–56d, and the water module and the soil module vial holders as illustrated in the block 326.

The measured tray calibration bar values for the Y direction edge 19d adjacent the receptacles 19c and 19e, respectively. Additionally, the ends of the bar 19 are used for location of the calibration bar 19 in the X direction, if desired. The end 19f adjacent the receptacle 19c can be sensed for positioning and skew in the X direction using the plunger 218, and programming the gripper head to move over that edge adjacent the corners so that the plunger would drop off the edge. The end edge 19g adjacent the receptacle 19e can be sensed by having a plunger to move to that edge and drop over the edge as well. This procedure of calibrating the position of the racks or trays and the orthogonality or orthogonal positions of the rows of the vial receptacles 31 shown in block 328.

After measurement, the calculated values for correction shown at block 330 for the orthogonality and the X-Y positions of each vial receptacle 31 are obtained.

The memory will correct the lookup table using the offset values from block 336 and other needed calculated values for orthogonality from block 330 and provide a working vial position lookup table indicated by the block 332, (if the default values were not corrected each time they were needed and retrieved). In other words there would be a working vial position lookup table generated in the software for the particular sequence of operations to be performed after the initial start up signal.

The calibration pad 17 default values from block 324 would be adjusted by measuring the values at the X edge and the Y edge as indicated by the block 334 and this information is used for the tray calibration functions of block 322.

The theoretical or default values for the stations 56a–56d, the water module, and soil module would be provided as indicated by block 336 and these values are adjusted with the offset values from block 336 and the calculated calibration pad values from block 334 to establish a working position table for the stations, and for the water and soil modules.

The robot arm would then be set to operate in a preprogrammed routine, or if desired, an individual sequence could be operator keyed in so that any particular vial in any of the receptacles 48a and 48b could be examined in sequence by lifting the vial, moving it to one of the receptacles 56a, 56b, 56c and 56d and subsequently as desired into the soil or water modules for analysis.

It can be seen thus that a position reference is provided at the "home" position, and in relation to a stored default controlled location the positions of the vial receptacles are provided. The actual position of the home is measured, by measuring the edges of the calibration pad, and the differences between the stored or default home position and the actual position or measured position are calculated, and then a corrected position of the vial holding stations is calculated as a function of the default position for that station and the differences that are calculated relating to the home position. The robotic arm is thus then operated and moved to the desired vial holding station as a function of the corrected or calculating position.

Figure 7:
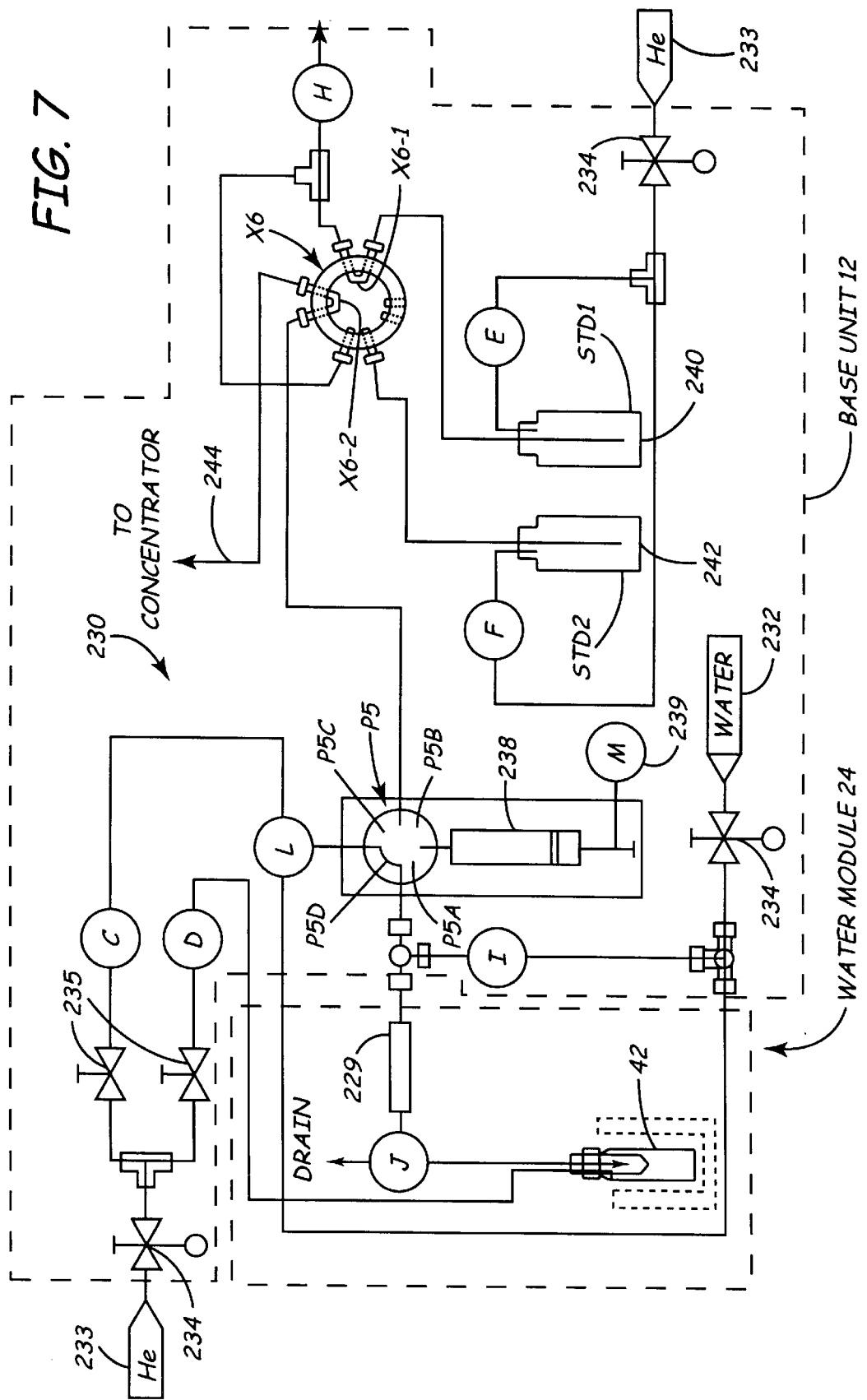
FIG. 7 is a diagrammatic view of a flow path of the device of FIG. 1 where only one sampling module is installed.

FIG. 7 schematically illustrates one arrangement used for sampling liquid or water samples in the station 20. Other sequences can be programmed for use with soil samples. Once a vial has been properly identified using the bar code reader, and equilibrated, and is placed by the vial transporter 28, into the cup type vial holder 82 of sampling module 24, sampling a liquid or water sample is conducted using the fluid circuit of FIG. 7. A sequence of operations for various functions is set forth in Table I, for simplicity of understanding of actuation or states of the various valves and other components.

In all of the sequences that are illustrated, it is important to note that the system permits backflushing the needles with a water or liquid to remove previous sample traces, utilizing the cup type vial holders to collect the backwash liquid and drain it as previously discussed and shown. A multi port chromatograph valve is utilized to permit selectively adding a known volume of two different standards into the test sample.

The samples are transferred to a purge and trap concentrator to purge the volatiles into a sorbet trap, which is then heated and swept with a carrier gas into a gas chromatograph column for separation and detection. Thus the outlet conduits labeled "to concentrator" means that these are connected to existing instruments that are well known for processing and subsequent analysis. A Model 3000 purge and trap concentrators made by Tekmar Company of Cincinnati, Ohio is useful or the spraying unit 100 can be used.

The water module connections and piping are shown generally at 230 and are outlined in dotted lines as are components on the base unit 12. A source of water 232, helium 233 and lines with pressure regulators 234 and flow controllers 235 are provided.

Figure 7A:
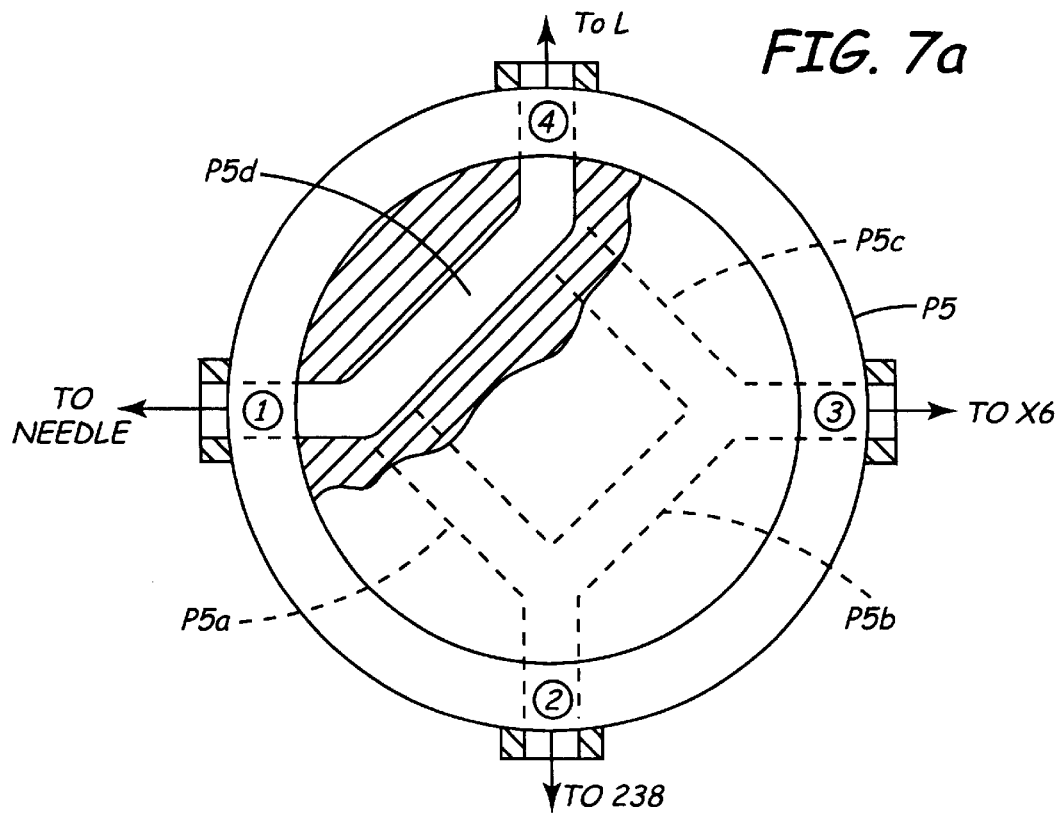
FIG. 7a is an enlarged schematic representation of a selector valve used in FIG. 7.

On-off valves C and D control a source of helium 233. Valve D connects to the outer needle assembly 92 in a water sample vial 42 held in vial holder 82. Valve C connects through a valve L to a solenoid operated multiple port valve P5 operated to four different connections in response to control signals to connect any two adjacent valve ports. For explanation purposes, the valve P5, also shown in FIGS. 1 and 7a, has a first position P5A that connects the ports 1 and 2; a second position P5B that connects ports 2 and 3; a third position P5C that connects ports 3 and 4, and as shown in FIG. 7 a fourth position P5D connecting ports 4 and 1. This valve is a conventional valve that has a center block that will connect the adjacent ports as desired by moving to the positions P5A, P5B, P5C, and P5D.

Port 2 of valve P5 is connected to a commercially available syringe pump 238 (See also FIG. 1) which has an inner plunger that is driven by an external motor 239 of any desired form. The syringe pump 238 receives and discharges samples under control of motor 239 when valve P5 is at its desired location.

Valve L connects to port 4 of valve P5, and port 1 is connected through a filter 239 to a valve J connected to the inner (sampling) needle of needle assembly 92 in vial 42. Valve I leads from the water source 232 to a "t" connection between filter 229 and valve P5. Valve L also has a port connected to the water source 232.

The port 2 of P5 connects to the outlet of the syringe pump 238. Port 3 of P5 connects to a port of a multi-port chromatographic valve X6, used for adding a known volume of a standard into a sample that is delivered to a concentrator such as the purge and trap concentrator.

A first standard source vial 240, and a second standard source vial 242 are fluidly coupled by conduits through valves E and F, respectively, to separate ports on valve X6. These vials can be used for providing matrix.

Figure 7B:
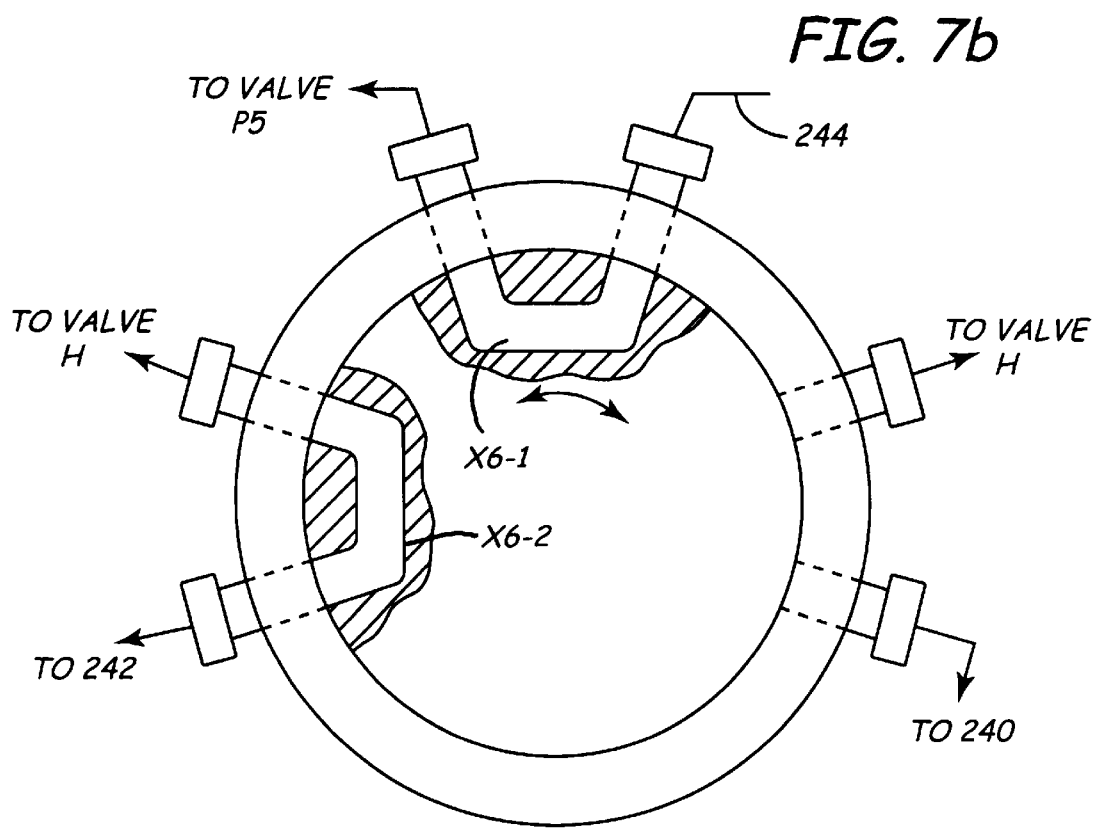
FIG. 7b is a schematic enlarged sectional view of a multi port chromatographic valve used in the flowpath of the present invention.

The multi port chromatographic valve X6 is a stepper type rotary solenoid valve that has an internal block that can be rotated 90°, and which has two schematically shown U-shaped internal channels X6-1 and X6-2 (see also FIG. 7b). Channel X6-1 connects the internal standard source 240 port to the port leading to valve H which leads to drain.

In FIG. 7 U-shaped channel X6-2 connects port 3 of valve P5 through a port of X6 to line 244. Valve X6 rotates 90° counter clockwise under control of circuit 66 and then as shown in FIG. 7b, channel X6-2 connects the surrogate standard source 242 to valve H. The U-shaped channel X6-1 then connects port 3 on valve P5 to line 244. Those are the two operable positions of valve X6.

The sequence of operation is shown in Table I below. In Table I the individual valves designated by capital letters are considered to have two positions. "0" designates off, and "1" equals on, in the table columns. The P5 valve connections or positions P5A–P5D, are designated by the letter (A–D) in the table column.

Valve X6 is indicated by position A shown in solid lines in FIG. 7, and in position B it is rotated 90° and shown in FIG. 7b. Additionally, in certain instances, the "vial mechanical position" column shows whether the vial holder and vial is up (U) (pierced by the sample needle) or down (D).

Standard filling is by opening valve H and valve E. Channel loop X6-1 fills with standard 1. Standard in loop X6-1 and one half of the sample are transferred by moving valve X6 90° to position "B" to connect channel X6-1 between valve P5 in position P5B and line 244. The syringe or pump 238 discharges ½ the sample through the valve X6 and line 244, carrying with it the quantity of standard 1 in channel X6-1 to line 244 and the concentrator.

Standard 2 is filled by moving valve P5 to position P5D, opening valves F and H (to drain) so a quantity of standard 2 fills loop X6-2. Transferring standard 2 occurs with valve P5 moved to position P5B, valve X6 moved to position A, and the remaining portion of the sample contained in the syringe or pump 238 discharged by motor 239 through loop X6-2 into line 244.

The two halves of the sample, and the different standards, (which can be selectively added) have thus been sent to the concentrator, for handling and for subsequent analysis. The transfer line is swept as valve C opens and valve P5 moves to the P5C position, connecting valve L to valve X6 and thus to line 244 for flushing through valve X-6.

The syringe is rinsed with water; valve I is open, valve J is open (to drain) and valve P5 is moved to the P5A position. The syringe is retracted to fill with water.

TABLE I

Water System - Water Module Only

| Mode of Operation | C | D | E | F | H | I | J | L | Vial Mech pos. | X6 | P5 |
|---|---|---|---|---|---|---|---|---|---|---|---|
| STANDBY AND WAIT FOR PURGE READY | 0 | 0 | 0 | 0 | 0 | 0 | 0 | 0 | D | A | D |
| PREPURGE | 1 | 1 | 0 | 0 | 0 | 0 | 0 | 0 | D | A | D |
| RAISE VIAL | 0 | 0 | 0 | 0 | 0 | 0 | 0 | 0 | U | A | D |
| FILL SYRINGE | 0 | 1 | 0 | 0 | 0 | 0 | 0 | 0 | U | A | A |
| FILL STD. 1 | 0 | 0 | 1 | 0 | 1 | 0 | 0 | 0 | U | A | A |
| TRANS SAMPLE STD 1 | 0 | 0 | 0 | 0 | 0 | 0 | 0 | 0 | U | B | B |
| SWEEP TRANS LINE | 1 | 0 | 0 | 0 | 0 | 0 | 0 | 0 | U | A | C |
| FILL STD 2 | 0 | 0 | 0 | 1 | 1 | 0 | 0 | 0 | U | B | D |
| TRANS SAMPLE STD 2 | 0 | 0 | 0 | 0 | 0 | 0 | 0 | 0 | U | A | B |
| SWEEP TRANS LINE | 1 | 0 | 0 | 0 | 0 | 0 | 0 | 0 | U | A | C |
| RINSE SYRINGE | 0 | 0 | 0 | 0 | 0 | 1 | 1 | 0 | U | A | A |
| DRAIN SYRINGE | 0 | 0 | 0 | 0 | 0 | 0 | 1 | 0 | U | A | A |
| BACKPLUSH FILTER | 0 | 0 | 0 | 0 | 0 | 1 | 1 | 0 | U | A | C |
| RETURN VIAL TO TRAY | 0 | 0 | 0 | 0 | 0 | 0 | 0 | 0 | D | A | C |
| FLUSHING NEEDLE | 0 | 0 | 0 | 0 | 0 | 1 | 0 | 0 | U | A | C |
| WAIT FOR DESORB | 0 | 0 | 0 | 0 | 0 | 0 | 0 | 0 | D | A | D |
| RINSE GLASSWARE | 0 | 0 | 0 | 0 | 0 | 0 | 0 | 1 | D | A | D |
| PURGE GLASSWARE | 1 | 0 | 0 | 0 | 0 | 0 | 0 | 0 | D | A | C |

At the cycle start (standby) and waiting for a purge ready signal from the concentrator or other instrument that it is ready to receive a sample the components are in the same condition. The vial is down, and valve P5 is in the solid line position P5D. In the prepurging stage, valves C and D open, and helium is provided through valves D, L, P5, and J to flow out the needles. The vial is raised to engage the needle, with the valves all closed. Filling the syringe as the syringe plunger retracts has valve D open and valve P5 shifted to position P5A connecting port 1 to port 2 to the syringe 238.

The syringe or pumper 238 is then drained by shutting off valve I but leaving valve J connected to drain and moving the syringe plunger up. The filter is backflushed by opening valves I and J and moving valve P5 in its P5C position.

The vial is lowered by operating the vial elevator and the vial transporter removes the vial from holder 82 and returns it to the tray. The vial holder 82 is preferably raised again and the inner needle is flushed with water by opening the valve I and leaving valve P5 in the P5C position. Water will flush through the inner needle to insure no carryover and will be contained and drained from the vial holder.

The needle may be purged if desired, through P5 by opening valve C with valve J off. While waiting for a desorb signal from the concentrator or test apparatus, the unit is essentially at rest with the valve P5 in its position P5D. The glassware conduits are liquid rinsed by opening the valve L to the water source, and connecting through valve P5 and valve X6 to line 244. The vial holder is down for reloading a vial. Helium is purged through the glassware by opening valve C after closing valve L and moving P5 to position P5C.

The cycle will then repeat, as desired for each additional vial that is lifted in the appropriate station for the water module.

It should be noted that if only one of the standards is injected into the sample per run, movement of valve X6 will place one of the channels X6-1 or X6-2 open to the other standard source, and such channel may then be flushed clean during the desorb cycle. The appropriate channel X6-1 or X6-2 is between valve P5 and line 244 during the syringe rinse and purge cycles.

Utilizing the soil module 26 is similar to that shown in FIG. 7 but will use a double ended vial 44, with a lower needle 130 and an upper double needle assembly. A single ended vial can be used. The valves and connections are selected to accommodate the needed functions for soil sample analysis.

The central control unit 66 is a standard programmable unit, such as a microcomputer or microprocessor that will accept inputs, including the needed limit sensors or limit switches for the soil module, and the water module indicating the limits of travel for the vial holders, a data entry keyboard, so that particular operations can be keyed in by an operator, inputs for the two switches indicating the vial racks are in position, limit switches for the x and y directions for the transfer arm, the two plungers on the gripper head for indicating position adjacent vial racks, and whether a vial is held in the gripper head. Three potentiometer inputs comprising encoders for the arm movement, including an encoder on the vertical moving drive for the gripper head, and bar code reader input for reading signals from the bar code labels for vial identification in handling are included.

The outputs would include operation of the pump or syringe motor 239, each of the solenoid valves that are shown in FIG. 7, the x, y, and z motors for the arm 156 as well as the actuator 200 for the gripper fingers, a motor for the rotating disc 62 at the bar code reader, the magnetic stir motor, and the elevator motors for the soil and water modules, respectively, as well as an output for the heater. All of these outputs can be provided in a desired sequence that can be preprogrammed into the unit, or modified by the data entry keyboard.

Such a programmable unit for the central circuit 66 is well known, and can form any desired type. The operations are sequential, so that the state of various solenoid valves and other operators are changed upon the completion of previous operations in the sequence. The x-y location of the vials in the vial racks can be programmed in, and the positioning of the vial holders for the soil and water module also can be preprogrammed in so that as instructions are given the vial transfer apparatus 28 will go to the proper location. The control sequences are more fully explained in connection with FIGS. 13, 14 and 15.

Modular operation is obtained, with a soil module, a water module or both. The additional valves also can be added with the modules. Valve X5 would be added to the base unit when both modules are used.

The water samples can be waste water or drinking water and rods or sludges can be handled. The bar code reader keeps track of the vials and samples, throughout the test and the controls can insure the results are attached to the proper sample by the bar code use. The bar code reader forms an input to control module 66 and control module can be used to correlate analysis with the appropriate vial. The cooling function for the vials is built into the base unit for convenient and proper test sequencing.

Although the present invention has been described with reference to preferred embodiments, workers skilled in the art will recognize that changes can be made in form and detail without departing from the spirit and scope of the invention.

What is claimed is:

1. In a vial autosampler having a plurality of vial holding stations and a robotic arm to carry a vial between the vial holding stations, a method of positioning the robotic arm relative to at least one of the vial holding stations comprising the steps of:

providing a position reference feature disposed at a fixed location with respect to the autosampler;

storing in memory a first nominal position for the at least one of the vial holding stations and a second nominal position for the position reference feature;

measuring an actual position of the position reference feature;

calculating a first difference between the second nominal position and the measured position of the position reference feature;

calculating a corrected position of the at least one of the vial holding stations as a function of the first nominal position and the first difference; and positioning the robotic arm as a function of the corrected position.

2. The method of claim 1 including providing a voltage indicating the actual position of the position reference feature relative to a fixed location on the vial autosampler representing the second nominal position.

3. The method of claim 2 wherein measuring the actual position of the position reference feature is done with a potentiometer, and wherein calculating the corrected position is based on an output signal of the potentiometer.

4. The method of claim 2 including calculating a scale of the provided voltage by calibrating the voltage indication relative to two locations in a path of travel of the robotic arm to determine a voltage value for each unit of travel between the two locations.

5. The method of claim 1, wherein the autosampler has removable and replaceable vial holding stations, and including the step of establishing the position of the removable vial holding stations when replaced on the autosampler by establishing distance from a reference edge at two locations and comparing differences in such distance to orient the replaced vial holding stations.

6. A method of calibrating movement of a robotic arm in a vial autosampler, the method comprising:

a) moving the robotic arm along a first axis until a first known location is reached;

b) obtaining an initial first sensor signal related to the first known location;

c) moving the robotic arm along the first axis until a second known location is reached;

d) obtaining a successive first sensor signal related to the second known location;

e) computing a first axis scale related to a difference between the initial and successive first sensor signals; and f) storing data based upon the first axis scale, wherein said data is used to calibrate movement of the robotic arm.

7. The method of claim 6, wherein the first sensor is a potentiometer.

8. The method of claim 6, wherein movement of the robotic arm during step c is in a direction opposite that during step a.

9. The method of claim 6, wherein the first known location corresponds to a position of a first location limit switch that indicates arrival of the robotic arm at the first known location.

10. The method of claim 6, wherein the second known location corresponds to a position of a second limit switch that indicates arrival of the robotic arm at the second known location.

11. The method of claim 6, and further comprising:

moving the robotic arm along a second axis orthogonal to the first axis until a third known location is reached;

obtaining an initial second sensor signal related to the third known location;

moving the robotic arm along the second axis until a fourth known location is reached;

obtaining a successive second sensor signal related to the fourth known location;

computing a second axis scale related to a difference between the initial and successive second sensor signals; and storing data based upon the second axis scale.

12. A method of calibrating movement of a robotic arm in a vial autosampler, the method comprising:

providing stored location information of a calibration feature disposed in a fixed location relative to the autosampler;

moving the robotic arm to the calibration feature;

measuring an actual location of the calibration feature; and calculating a calibrated home position based upon a comparison of the stored location information and the measured actual location.

13. The method of claim 12, wherein measuring the actual location of the calibration feature includes:

bringing the robotic arm into contact with the calibration feature;

moving the robotic arm in a first direction while contacting the calibration feature until loss of contact is registered;

bringing the robotic arm into contact with the calibration feature again; and moving the robotic arm in a second direction orthogonal to the first direction while in contact with the calibration feature until loss of contact is measured.

14. A method of calibrating movement of a robotic arm in a vial autosampler, the method comprising:

positioning a calibration bar relative to at least two vial storage locations;

bringing the robotic arm into contact with the calibration bar;

monitoring contact between the bar and the robotic arm while the robotic arm is moved relative to the bar in order to detect loss of contact between the bar and the robotic arm; and calculating a calibration parameter based upon the movement of the robotic arm relative to the bar, and the detected loss of contact.

15. The method of claim 14, wherein positioning the bar relative to at least two vial storage locations includes coupling at least a pair of plugs on the bar with at least a pair of vial receptacles in the autosampler.

16. The method of claim 14, wherein monitoring contact between the bar and the robotic arm further includes:

moving the robotic arm to a first position on the bar;

moving the robotic arm along a first axis until a sensor signal registers loss of contact between the bar and the robotic arm at a second position;

moving the robotic arm to a third position spaced from the first position along an axis orthogonal to the first axis; and moving the robotic arm along the first axis until a sensor signal registers loss of contact between the bar and the robotic arm at a fourth position.

17. The method of claim 16, wherein the calibration parameter is relative skew between a tray containing the at least two vial storage locations and the robotic arm.

18. A method of calibrating motion of a robotic arm in a vial autosampler, the method comprising:

measuring axis scaling factors in at least two orthogonal axes;

determining a calibrated home point using the axis scaling factors and a calibration reference feature;

measuring relative skew of a sample tray with respect to the vial autosampler; and compensating stored vial receptacle position information based upon the home point and the measured skew.

* * * * *